(12) United States Patent
D'Angelo

(10) Patent No.: US 12,239,656 B2
(45) Date of Patent: Mar. 4, 2025

(54) NUCLEOPORINS AS DRUG TARGETS FOR ANTI-PROLIFERATIVE THERAPEUTICS

(71) Applicant: Sanford Burnham Prebys Medical Discovery Institute, La Jolla, CA (US)

(72) Inventor: Maximiliano D'Angelo, San Diego, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 18/058,212

(22) Filed: Nov. 22, 2022

(65) Prior Publication Data

US 2023/0172964 A1 Jun. 8, 2023

Related U.S. Application Data

(63) Continuation of application No. 16/629,463, filed as application No. PCT/US2018/041461 on Jul. 10, 2018, now Pat. No. 11,564,937.

(60) Provisional application No. 62/531,257, filed on Jul. 11, 2017.

(51) Int. Cl.
| | |
|---|---|
| *C07H 21/02* | (2006.01) |
| *A61K 31/7105* | (2006.01) |
| *A61K 35/00* | (2006.01) |
| *C07H 21/04* | (2006.01) |
| *C12N 15/113* | (2010.01) |
| *G01N 33/50* | (2006.01) |
| *A61K 45/06* | (2006.01) |

(52) U.S. Cl.
CPC .......... *A61K 31/7105* (2013.01); *A61K 35/00* (2013.01); *C12N 15/113* (2013.01); *G01N 33/5011* (2013.01); *A61K 45/06* (2013.01); *C12N 2310/122* (2013.01); *C12N 2310/141* (2013.01)

(58) Field of Classification Search
CPC .......... C12N 15/113; C12N 2310/14
See application file for complete search history.

(56) References Cited

U.S. PATENT DOCUMENTS

| 11,564,937 B2 | 1/2023 | D'Angelo |
| 2010/0273859 A1 | 10/2010 | Elledge et al. |
| 2015/0023973 A1 | 1/2015 | Kwon et al. |

FOREIGN PATENT DOCUMENTS

| WO | WO-2018129080 A1 | 7/2018 |
| WO | WO-2019014234 A1 | 1/2019 |

OTHER PUBLICATIONS

Chen et al, PAK6 increase chemoresistance and is a prognostic marker for stage II and III colon cancer patients undergoing 5-FU based chemotherapy. Oncotarget. 6(1):355-367 (2015).
David-Watine. Silencing nuclear pore protein Tpr elicits a senescent-like phenotype in cancer cells. PLoS One 6(7):e22423 (2011).
Elbashir et al. Functional anatomy of siRNAs for mediating efficient RNAi in *Drosophila melanogaster* embryo lysate. EMBO J. 20(23):6877-88 (2001).
Higby et al., 5-Flurouracil disrupts nuclear export and nuclear pore permeability in a calcium dependent manner. Apoptosis. 22(3):393-405 (2017).
Karacosta et al., Nucleoporin 62 and Ca(2+)/calmodulin dependent kinase kinase 2 regulate androgen receptor activity in castrate resistant prostate cancer cells. Prostate 76:294-306 (2016).
MacDiarmid et al. Sequential treatment of drug-resistant tumors with targeted minicells containing siRNA or a cytotoxic drug. Nat Biotechnol. 27(7):643-51 (2009).
PCTUS2018041461 International Search Report and Written Opinion dated Nov. 1, 2018.
PCT/US2018/041461 Invitation to Pay Additional Fees dated Sep. 7, 2018.
Prior et al. A comprehensive survey of ras mutations in cancer. Cancer Res 72:2457-2467 (2012).
Simon et al. Cancer and the Nuclear Pore Complex. In: Schirmer E., de las Heras J. (eds) Cancer Biology and the Nuclear Envelope. Advances in Experimental Medicine and Biology, vol. 773. Springer, New York, NY. (2014).
U.S. Appl. No. 16/629,463 Office Action dated Apr. 19, 2022.
U.S. Appl. No. 16/629,463 Office Action dated Sep. 7, 2021.
Sakuma, Stephen et al. Inhibition of Nuclear Pore Complex Formation Selectively Induces Cancer Cell Death. Cancer Discov 11(1):176-193 (2021).

*Primary Examiner* — Amy Rose Hudson
(74) *Attorney, Agent, or Firm* — WILSON SONSINI GOODRICH & ROSATI

(57) ABSTRACT

Disclosed herein are methods of inhibiting nuclear pore complex assembly and inducing nuclear pore complex disassembly. Methods to screen for agents that inhibit nuclear pore assembly or induce nuclear pore complex disassembly are also disclosed.

13 Claims, 24 Drawing Sheets

Endogenous Nup62 tagged with GFP

HT-29 Colorectal adenocarcinoma xenografts tumors

HT-29 Colorectal adenocarcinoma xenografts tumors

A375 Skin Melanoma xenografts tumors

NUCLEOPORINS AS DRUG TARGETS FOR ANTI-PROLIFERATIVE THERAPEUTICS

CROSS-REFERENCE

This application is a continuation of U.S. National Stage application Ser. No. 16/629,463, filed on Jan. 8, 2020; claiming priority to International Application No. PCT/US2018/041461, filed on Jul. 10, 2018; and claims the benefit of U.S. Provisional Application No. 62/531,257, filed Jul. 11, 2017, the entirety of which is hereby incorporated by reference herein.

SUMMARY OF THE INVENTION

Disclosed herein, in some embodiments, are methods of treating a proliferative disease or disorder in an individual in need thereof, comprising: administering to the individual a therapeutically effective amount of an agent that inhibits nuclear pore complex assembly, induces nuclear pore complex disassembly, or inhibits nuclear pore complex function. In some instance, the agent inhibits expression of a component of the nuclear pore complex. In some instances, the agent promotes degradation of a component of the nuclear pore complex. In some instances, the agent inhibits function of a component of the nuclear pore complex. In some instances, the agent modulates the expression of a regulator of the nuclear pore complex assembly. In some instances, the agent inhibits expression of a regulator of the nuclear pore complex assembly. In some instances, the agent inhibits expression of a positive regulator of the nuclear pore complex assembly. In some instances, the agent induces expression of a regulator of the nuclear pore complex assembly. In some instances, the agent induces the expression of negative regulator of the nuclear pore complex assembly. In some instances, the agent modulates the function of a regulator of the nuclear pore complex assembly. In some instances, the agent inhibits function of a regulator of the nuclear pore complex assembly. In some instances, the agent inhibits function of a positive regulator of the nuclear pore complex assembly. In some instances, the agent induces function of a regulator of the nuclear pore complex assembly. In some instances, the agent induces the function of negative regulator of the nuclear pore complex assembly. In some instances, the agent modulates the expression of a regulator of the nuclear pore complex disassembly. In some instances, the agent induces expression of a regulator of the nuclear pore complex disassembly. In some instances, the agent induces expression of a positive regulator of the nuclear pore complex disassembly. In some instances, the agent inhibits expression of a regulator of the nuclear pore complex disassembly. In some instances, the agent inhibits the expression of negative regulator of the nuclear pore complex disassembly. In some instances, the agent modulates the function of a regulator of the nuclear pore complex disassembly. In some instances, the agent induces function of a regulator of the nuclear pore complex disassembly. In some instances, the agent induces function of a positive regulator of the nuclear pore complex disassembly. In some instances, the agent inhibits function of a regulator of the nuclear pore complex disassembly. In some instances, the agent inhibits the function of negative regulator of the nuclear pore complex disassembly. In some instances, the agent inhibits Nup35, Nup37, Nup43, Nup45, Nup50, Nup54, Nup58 (Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits the expression of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits the function of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits the transport of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1 (Nup12), Aladin, TPR, GLE1, and ELYS of the nuclear pore complex. In some instances, the agent inhibits the binding of Nup35, Nup37, Nup43, Nup45, Nup50, Nup54, Nup58 (Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex to other components of the nuclear pore complex. In some instances, the agent inhibits Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1 (Nup12), Aladin, TPR, or Elys of the nuclear pore complex. In some instances, the agent inhibits expression of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the agent inhibits function of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the agent inhibits transport of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1 (Nup12), Aladin, TPR, or Elys of the nuclear pore complex. In some instances, the agent inhibits binding of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex to other components of the nuclear pore complex. In some instances, the agent is a small molecule. In some instances, the agent is a small interfering RNA (siRNA). In some instances, the agent is a short hairpin RNA (shRNA). In some instances, the agent is a microRNA (miRNA). In some instances, the agent is a messenger RNA (mRNA). In some instances, the agent is a guideRNA (gRNA). In some instances, the method further comprises administering an additional therapeutic agent. In some instances, the agent and the additional therapeutic agent are administered simultaneously. In some instances, the agent and the additional therapeutic agent are administered sequentially. In some instances, the agent is administered before administering the additional therapeutic agent. In some instances, the agent is administered after administering the additional therapeutic agent. In some instances, the disease or disorder is a neoplastic disease. In some instances, the disease or disorder is caused by a malignant cell. In some instances, the disease or disorder is an inflammatory disease. In some instances, the disease or disorder is cancer. In some instances, the cancer has a mutation in the Ras gene. In some instances, the mutation is a G12D mutation.

Disclosed herein, in some embodiments, is a pharmaceutical composition, comprising (a) an agent that inhibits nuclear pore complex assembly, induces nuclear pore complex disassembly, or inhibits nuclear pore complex function; and (b) a pharmaceutically acceptable excipient. In some instances, the agent inhibits expression of a component of the nuclear pore complex. In some instances, the agent promotes degradation of a component of the nuclear pore complex. In some instances, the agent inhibits function of a component of the nuclear pore complex. In some instances, the agent modulates the expression of a regulator of the nuclear pore complex assembly. In some instances, the agent inhibits expression of a regulator of the nuclear pore complex assembly. In some instances, the agent inhibits expression of a positive regulator of the nuclear pore complex assembly. In some instances, the agent induces expression of a regulator of the nuclear pore complex assembly. In some instances, the agent induces the expression of negative regulator of the nuclear pore complex assembly. In some instances, the agent modulates the function of a regulator of the nuclear pore complex assembly. In some instances, the agent inhibits function of a regulator of the nuclear pore complex assembly. In some instances, the agent inhibits function of a positive regulator of the nuclear pore complex assembly. In some instances, the agent induces function of a regulator of the nuclear pore complex assembly. In some instances, the agent induces the function of negative regulator of the nuclear pore complex assembly. In some instances, the agent modulates the expression of a regulator of the nuclear pore complex disassembly. In some instances, the agent induces expression of a regulator of the nuclear pore complex disassembly. In some instances, the agent induces expression of a positive regulator of the nuclear pore complex disassembly. In some instances, the agent inhibits expression of a regulator of the nuclear pore complex disassembly. In some instances, the agent inhibits the expression of negative regulator of the nuclear pore complex disassembly. In some instances, the agent modulates the function of a regulator of the nuclear pore complex disassembly. In some instances, the agent induces function of a regulator of the nuclear pore complex disassembly. In some instances, the agent induces function of a positive regulator of the nuclear pore complex disassembly. In some instances, the agent inhibits function of a regulator of the nuclear pore complex disassembly. In some instances, the agent inhibits the function of negative regulator of the nuclear pore complex disassembly. In some instances, the agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits the expression of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits the function of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits the transport of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1 (Nup12), Aladin, TPR, GLE1, and ELYS of the nuclear pore complex. In some instances, the agent inhibits the binding of Nup35, Nup37, Nup43, Nup45, Nup50, Nup54, Nup58 (Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex to other components of the nuclear pore complex. In some instances, the agent inhibits Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1 (Nup12), Aladin, TPR, or Elys of the nuclear pore complex. In some instances, the agent inhibits expression of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the agent inhibits function of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the agent inhibits transport of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1 (Nup12), Aladin, TPR, or Elys of the nuclear pore complex. In some instances, the agent inhibits binding of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex to other components of the nuclear pore complex. In some instances, the agent is a small molecule. In some instances, the agent is a small interfering RNA (siRNA). In some instances, the agent is a short hairpin RNA (shRNA). In some instances, the agent is a microRNA (miRNA). In some instances, the agent is a messenger RNA (mRNA). In some instances, the agent is a guideRNA (gRNA). In some instances, the composition further comprises an additional therapeutic agent. In some instances, the additional therapeutic agent is an anti-proliferative agent. In some instances, the additional therapeutic agent is anti-cancer agent. In some instances, the additional therapeutic agent is a chemotherapeutic agent. In some instances, the additional therapeutic agent is a hormonal agent.

Disclosed herein, in some embodiments, are methods of screening for a therapeutic agent for treating a proliferative disease or disorder in an individual in need thereof, the method comprising: (a) contacting a cell with a test agent; (b) detecting (i) inhibition of nuclear pore complex assembly as compared to a control; or (ii) induction of nuclear pore complex disassembly as compared to a control; and (c) identifying the test agent as a therapeutic agent if the test agent reduces the number of nuclear pore complexes in the cell as compared to the control. In some instances, the cell is a tumor cell in vitro. In some instances, the cell is a tumor cell in vivo. In some instances, step (b) comprises performing: (i) cell proliferation or survival assay in vitro; and (ii) tumor development, growth or metastasis assay in vivo. In some instances, the detection is by direct visualization. In some instances, the detection is by microscopy imaging, Western blot, immunohistochemistry, ELISA, SPARCL, fluorescent signal detector, chromatography, radioactive binding assay, a fluorescence binding assay, mass spectrometry, a kinetic exclusion assay, a crystallography assay, or live imaging. In some instances, the therapeutic agent is a small molecule. In some instances, the therapeutic agent is a small interfering RNA (siRNA). In some instances, the therapeutic agent is a short hairpin RNA (shRNA). In some instances, the therapeutic agent is a microRNA (miRNA). In some instances, the therapeutic agent is a messenger RNA (mRNA). In some instances, the therapeutic agent is a guideRNA (gRNA). In some instances, the therapeutic agent is an antisense oligonucleotide. In some instances, the therapeutic agent is a peptide. In some instances, the therapeutic agent is a peptidomimetic. In some instances, the therapeutic agent is an aptamer. In some instances, the therapeutic agent targets a component of the nuclear pore complex. In some instances, the therapeutic agent inhibits expression of a component of the nuclear pore complex. In some instances, the therapeutic agent promotes degradation of a component of the nuclear pore complex. In some instances, the therapeutic agent inhibits function of a component of the nuclear pore complex. In some instances, the therapeutic agent modulates the expression of a regulator of the nuclear pore complex assembly. In some instances, the therapeutic agent inhibits expression of a regulator of the nuclear pore complex assembly. In some instances, the therapeutic agent inhibits expression of a positive regulator of the nuclear pore complex assembly. In some instances, the therapeutic agent induces expression of a regulator of the nuclear pore complex assembly. In some instances, the therapeutic agent induces the expression of negative regulator of the nuclear pore complex assembly. In some instances, the therapeutic agent modulates the function of a regulator of the nuclear pore complex assembly. In some instances, the therapeutic agent inhibits function of a regulator of the nuclear pore complex assembly. In some instances, the therapeutic agent inhibits function of a positive regulator of the nuclear pore complex assembly. In some instances, the therapeutic agent induces function of a regulator of the nuclear pore complex assembly. In some instances, the therapeutic agent induces the function of negative regulator of the nuclear pore complex assembly. In some instances, the therapeutic agent modulates the expression of a regulator of the nuclear pore complex disassembly. In some instances, the therapeutic agent induces expression of a regulator of the nuclear pore complex disassembly. In some instances, the therapeutic agent induces expression of a positive regulator of the nuclear pore complex disassembly. In some instances, the therapeutic agent inhibits expression of a regulator of the nuclear pore complex disassembly. In some instances, the therapeutic agent inhibits the expression of negative regulator of the nuclear pore complex disassembly. In some instances, the therapeutic agent modulates the function of a regulator of the nuclear pore complex disassembly. In some instances, the therapeutic agent induces function of a regulator of the nuclear pore complex disassembly. In some instances, the therapeutic agent induces function of a positive regulator of the nuclear pore complex disassembly. In some instances, the therapeutic agent inhibits function of a regulator of the nuclear pore complex disassembly. In some instances, the therapeutic agent inhibits the function of negative regulator of the nuclear pore complex disassembly. In some instances, the therapeutic agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the expression of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the function of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the transport of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the binding of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex to other components of the nuclear pore complex. In some instances, the therapeutic agent inhibits Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits expression of Nup35, Nup37, Nup43, Nup45, Nup50, Nup54, Nup58 (Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits function of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits transport of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits binding of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex to other components of the nuclear pore complex. In some instances, the therapeutic agent targets a component of the nuclear pore complex comprising a protein binding/interacting pair, thereby disrupting the pair. In some instances, the protein binding/interacting pair is selected from a pair listed in Table 1. In some instances, the protein binding/interacting pair is selected from a pair listed in Table 2. In some instances, the protein binding/interacting pair is selected from a pair listed in Table 3. In some instances, the therapeutic agent targets the RNA or DNA of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1 (Nup12), Aladin, TPR, GLE1, and ELYS of the nuclear pore complex. In some instances, the therapeutic agent binds to Nup35, Nup37, Nup43, Nup45, Nup50, Nup54, Nup58 (Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex.

Disclosed herein, in some embodiments, are methods of screening for a therapeutic agent for treating a proliferative disease or disorder in an individual in need thereof, the method comprising: (a) contacting a cell with a test agent; (b) detecting inhibition of nuclear transport as compared to a control; and (c) identifying the test agent as a therapeutic agent if the test agent reduces the expression or activity of a component of nuclear pore complex in the cell as compared to the control. In some instances, the cell is a tumor cell in vitro. In some instances, the cell is a tumor cell in vivo. In some instances, step (b) comprises performing: (i) cell proliferation or survival assay in vitro; and (i) tumor development, growth or metastasis assay in vivo. In some instances, the expression or activity of the component is measured by microscopy imaging, Western blot, immunohistochemistry, ELISA, SPARCL, fluorescent signal detector, chromatography, radioactive binding assay, a fluorescence binding assay, mass spectrometry, a kinetic exclusion assay, a crystallography assay, PCR, or gel electrophoresis. In some instances, the therapeutic agent is a small molecule. In some instances, the therapeutic agent is a small interfering RNA (siRNA). In some instances, the therapeutic agent is a short hairpin RNA (shRNA). In some instances, the therapeutic agent is a microRNA (miRNA). In some instances, the therapeutic agent is a messenger RNA (mRNA). In some instances, the therapeutic agent is a guideRNA (gRNA). In some instances, the therapeutic agent is an antisense oligonucleotide. In some instances, the therapeutic agent is a peptide. In some instances, the therapeutic agent is a peptidomimetic. In some instances, the therapeutic agent is an aptamer. In some instances, the therapeutic agent targets a component of the nuclear pore complex. In some instances, the therapeutic agent inhibits expression of a component of the nuclear pore complex. In some instances, the therapeutic agent promotes degradation of a component of the nuclear pore complex. In some instances, the therapeutic agent inhibits function of a component of the nuclear pore complex. In some instances, the therapeutic agent modulates the expression of a regulator of the nuclear pore complex assembly. In some instances, the therapeutic agent inhibits expression of a regulator of the nuclear pore complex assembly. In some instances, the therapeutic agent inhibits expression of a positive regulator of the nuclear pore complex assembly. In some instances, the therapeutic agent induces expression of a regulator of the nuclear pore complex assembly. In some instances, the therapeutic agent induces the expression of negative regulator of the nuclear pore complex assembly. In some instances, the therapeutic agent modulates the function of a regulator of the nuclear pore complex assembly. In some instances, the therapeutic agent inhibits function of a regulator of the nuclear pore complex assembly. In some instances, the therapeutic agent inhibits function of a positive regulator of the nuclear pore complex assembly. In some instances, the therapeutic agent induces function of a regulator of the nuclear pore complex assembly. In some instances, the therapeutic agent induces the function of negative regulator of the nuclear pore complex assembly. In some instances, the therapeutic agent modulates the expression of a regulator of the nuclear pore complex disassembly. In some instances, the therapeutic agent induces expression of a regulator of the nuclear pore complex disassembly. In some instances, the therapeutic agent induces expression of a positive regulator of the nuclear pore complex disassembly. In some instances, the therapeutic agent inhibits expression of a regulator of the nuclear pore complex disassembly. In some instances, the therapeutic agent inhibits the expression of negative regulator of the nuclear pore complex disassembly. In some instances, the therapeutic agent modulates the function of a regulator of the nuclear pore complex disassembly. In some instances, the therapeutic agent induces function of a regulator of the nuclear pore complex disassembly. In some instances, the therapeutic agent induces function of a positive regulator of the nuclear pore complex disassembly. In some instances, the therapeutic agent inhibits function of a regulator of the nuclear pore complex disassembly. In some instances, the therapeutic agent inhibits the function of negative regulator of the nuclear pore complex disassembly. In some instances, the therapeutic agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the expression of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the function of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the transport of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent inhibits the binding of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex to other components of the nuclear pore complex. In some instances, the therapeutic agent inhibits Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1 (Nup12), Aladin, TPR, or Elys of the nuclear pore complex. In some instances, the therapeutic agent inhibits expression of Nup35, Nup37, Nup43, Nup45, Nup50, Nup54, Nup58 (Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits function of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits transport of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex. In some instances, the therapeutic agent inhibits binding of Nup35, Nup37, Nup43, Nup45, Nup50, Nup54, Nup58(Nup11), Nup62, Nup75/85, Nup93, Nup96, Nup107, Nup133, Nup155, Nup160, Nup358(RanBP2), Seh1, Sec13, NDC1, Pom121, Nup210, RAE1, HCG1/CG1(Nup12), Aladin, TPR, or Elys of the nuclear pore complex to other components of the nuclear pore complex. In some instances, the therapeutic agent targets a component of the nuclear pore complex comprising a protein binding/interacting pair, thereby disrupting the pair. In some instances, the protein binding/interacting pair is selected from a pair listed in Table 1. In some instances, the protein binding/interacting pair is selected from a pair listed in Table 2. In some instances, the protein binding/interacting pair is selected from a pair listed in Table 3. In some instances, the therapeutic agent targets the RNA or DNA of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1 (Nup12), Aladin, TPR, GLE1, and ELYS of the nuclear pore complex. In some instances, the therapeutic agent binds to Nup35, Nup37, Nup43, Nup45, Nup50, Nup54, Nup58 (Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8A exemplifies the recovery of the Tomato signal inside the nucleus after photobleaching. FIG. 8B exemplifies a quantification of the fluorescent signal for the Tomato reporter 1 min after photobleaching. Inhibition of nuclear pore complex assembly blocks nuclear import.

FIG. 14A shows a representative image of tumors carrying control or Nup160 shRNAs, untreated or treated with doxycycline to induce shRNA and inhibition of nuclear pore assembly. FIG. 14B is an exemplary quantification of tumor volume after treatment in doxycycline-treated control and Nup160 shRNA carrying tumors.

FIG. 18A shows a representative image of tumors carrying control or Nup160 shRNAs. Inhibition of nuclear pore assembly strongly inhibits tumor growth and results in tumor remission. FIG. 18B is an exemplary quantification of tumor weight after treatment in doxycycline-treated control and Nup160 shRNA carrying tumors.

FIG. 19A exemplifies images of luciferase signal in live mice at 1, 5 and 9 days after injection. Positive signal denotes tumor formation. The luciferase signal over time in animals injected with B16F10 mouse melanoma cells was quantified (FIG. 19B). FIG. 19B is an exemplary quantification of luciferase signal at different days post-injection of B16F10 cells.

FIG. 21A exemplifies that A375 grow faster than IMR90 and are more sensitive to nuclear pore complex inhibition. IMR90 cells numbers are not significantly affected by inhibition of nuclear pore assembly during the duration of treatment which completely eliminates the A375 melanoma cells. FIG. 21B is an exemplary magnification of the vertical axes to depict the lower effect of nuclear pore complex assembly inhibition for normal cells.

FIG. 22A illustrates that cells carrying wild type (WT) or mutant Ras (MT) where treated with shRNAs to inhibit nuclear pore assembly (shN1) and cell proliferation over time was compared to control-treated cells (shSC). FIG. 22B illustrates the number of shN1-treated cells to control cells determined over time and shown as percentage. Ras mutant cells show a significant higher inhibition of cell proliferation than Ras wild type cells.

DETAILED DESCRIPTION OF THE INVENTION

Figure 1:
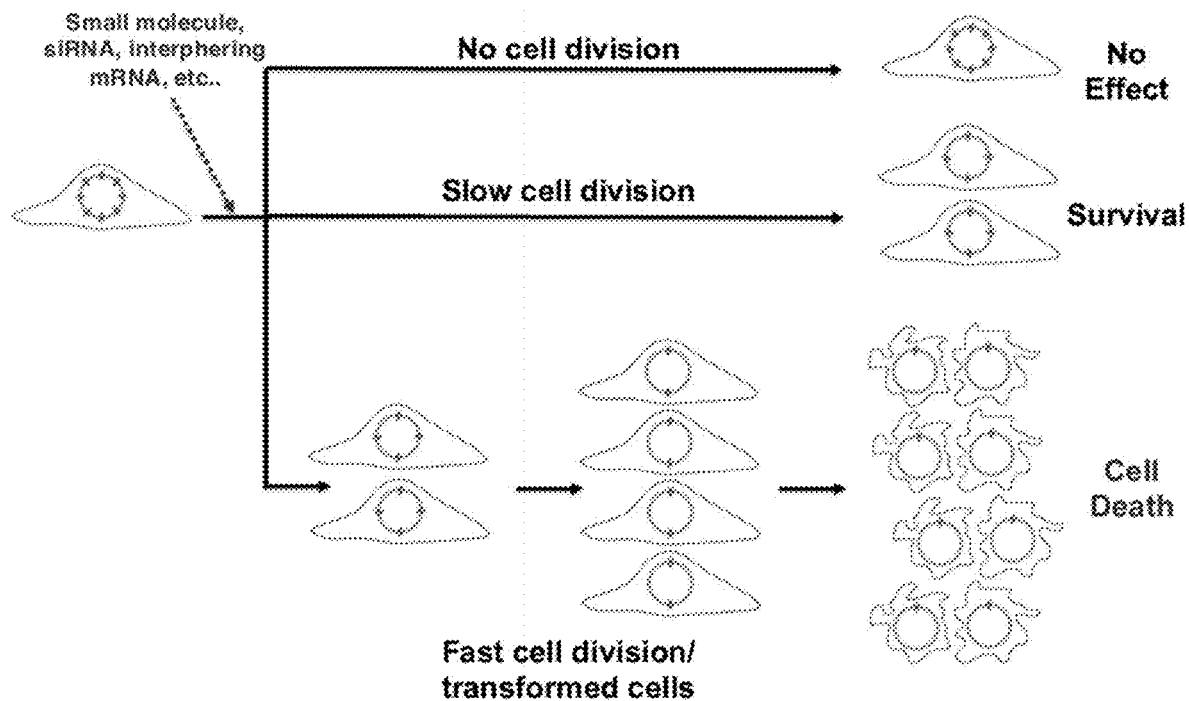
FIG. 1 is a model exemplifying how inhibition of nuclear pore complex (NPC) assembly affects the survival of cells with different proliferating rates. In addition to having higher proliferation rates, transformed cells are addicted to the nuclear transport machinery which makes them even more sensitive to the inhibition of NPC assembly.

Disclosed herein, in some embodiments, are methods of treating a proliferative disease or disorder in an individual in need thereof, comprising: administering to the individual a therapeutically effective amount of an agent that inhibits nuclear pore complex assembly, induces nuclear pore complex disassembly; or inhibits nuclear pore complex function.

Disclosed herein, in some embodiments, are also methods of screening for a therapeutic agent for treating a proliferative disease or disorder, the method comprising: (a) contacting a cell with a test agent; (b) detecting (i) inhibition of nuclear pore complex assembly as compared to a control; or (ii) induction of nuclear pore complex disassembly as compared to a control; and (c) identifying the test agent as a therapeutic agent if the test agent reduces the number of nuclear pore complexes in the cell as compared to the control. The methods disclosed herein, further comprises screening for a therapeutic agent for treating a proliferative disease or disorder, the method comprising: (a) contacting a cell with a test agent; (b) detecting inhibition of nuclear transport as compared to a control; and (c) identifying the test agent as a therapeutic agent if the test agent reduces the expression, levels, or activity of a component of nuclear pore complex in the cell as compared to the control.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error, e.g., ±5%, ±10%, or ±15%.

The section headings used herein are for organizational purposes only and are not to be construed as limiting the subject matter described.

As used herein, the terms "individual(s)", "subject(s)" and "patient(s)" are used interchangeably and mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. For example the term "treat" or "treating" with respect to a proliferative disorder refers to stopping the progression of said disorder, slowing down, or amelioration of symptoms associated with the presence of said cells, causing apoptosis of cells causing the disorder. Treatment of an individual suffering from a proliferative disease or disorder refers to a decrease and elimination of the cells causing the disease in an individual. For example, a decrease or elimination of tumor cells in an individual suffering from cancer.

By "therapeutically effective amount" is meant an amount of a compound described herein effective to yield the desired therapeutic response. For example, an amount effective to inhibit nuclear pore complex assembly, induce nuclear pore complex disassembly or inhibit nuclear pore complex function, thereby targeting the cells causing the disorder. The therapeutically effective amount will vary with such factors as the particular condition being treated, the physical condition of the patient, the type of mammal or animal being treated, the duration of the treatment, the nature of concurrent therapy (if any), and the specific formulations employed and the structure of the agents or its derivatives.

Nuclear Pore Complex

A hallmark of human cells is that the chromosomes (DNA) are housed inside a membrane structure known as the cell nucleus. The nucleus has all the genetic material and is considered the control center of the cell. In order to regulate the activity of genes in the DNA inside the nucleus, cells need to be able to move molecules in and out of this compartment. Nuclear pore complexes (NPCs) are large protein channels that act as the doors of the nucleus. NPCs are multiprotein complexes built from 33 different proteins known as nucleoporins. These channels represent the gateway into the nuclear compartment and control the entrance and exit of all molecules in a highly regulated and efficient manner. Since numerous proteins, including oncogenes and tumor suppressors, need to access the genome to perform their functions, alterations in the nuclear transport machinery are observed in cancer cells. No inhibitors of the nuclear pore complexes have been developed or tested as antineoplastic or antiproliferative agents. In some instances, targeting the activity of the nuclear transport machinery affects the survival of cancer cells. In some instances, targeting the activity of the nuclear transport machinery affects the survival of excessively proliferative cells.

Inhibition of nuclear pore complex assembly, instead of the nucleocytoplasmic transport process, is beneficial for the treatment of disorders, such as neoplastic and proliferative disorders, for several reasons. First, differently from nucleocytoplasmic transport, nuclear pore complex assembly is restricted to proliferating cells. Thus, blocking this process does not affect non-dividing cells, such as neurons, or muscle, which minimizes its effect on normal tissues and reduces undesired toxicity. Second, since inhibition of nuclear pore complex assembly only occurs during cell division, cells that divide more, faster or are more addicted to nuclear transport, such as malignant cells, are specifically and more strongly affected. Third, in cancer and other proliferative diseases, malignant cells show upregulated cell division either by misregulation of cell proliferation factors, the inhibition of cell death pathways, or both. To control these processes, cells still need to regulate the activity of genes inside the nucleus. Elimination of the transport channels that allow the movement of molecules in and out of the nucleus is incompatible with the function of these cells and affects abnormally proliferating cells independently of the processes or pathways that they have mutated. Therefore, a therapy based on nuclear pore complex assembly inhibition is effective in a widespread of proliferative and neoplastic diseases independently of their causes. Fourth, many current therapies for neoplastic or other proliferative disorders rely on inhibiting different signaling pathways, either at the level of surface receptors (such as EGFR inhibitors), or downstream effectors of the signaling cascades (e.g. ERK and ALK inhibitors). An important and very common problem that these therapies face is the rapid appearance of resistant cells, which loose the sensitivity to the inhibitors. In many cases, cells overcome the effect of the inhibitors by switching to, or over-activating, a different signaling pathway. But because all signaling pathways result in the activation/repression of genes inside the nucleus and, thus, necessarily require molecules to enter and exit nucleus, eliminating the doors to the nucleus (namely nuclear pore complexes) by inhibiting their assembly prevents the cells on using other signaling cascades to overcome inhibition. Therefore, inhibiting nuclear pore complex assembly has a strong effect on the survival of highly proliferating cells with significantly lower chances of resistance than conventional approaches based on the inhibition of cell signaling. In some embodiments, the present disclosure exemplifies that inhibiting the assembly of nuclear pore complexes: 1) reduces proliferation and induces death in cancer cells without significantly affecting cells that do not divide or divide less frequently; 2) inhibits tumor growth; 3) induces cancer cell death within the tumor; and 4) results in tumor remission and strongly reduces tumor size in animals.

In the same way as nuclear pore complex assembly, disassembly of this structure only takes place in dividing cells. Stimulating the process of nuclear pore complex disassembly in dividing cells also results in the same reduction in nuclear pore complexes and affects the proliferation and survival of malignant cells as disclosed above. Identifying regulators of nuclear pore complex disassembly is also a promising strategy for the treatment of proliferative diseases. In some instances, inhibiting nuclear pore complex assembly, inducing nuclear pore complex disassembly, and inhibiting nuclear pore complex function by targeting different nuclear pore complex components triggers cell death of excessively proliferating cells. In some instances, inhibiting nuclear pore complex assembly, inducing nuclear pore complex disassembly, and inhibiting nuclear pore complex function by targeting different nuclear pore complex components triggers cell death in cancer cells. In some instances, inhibiting nuclear pore complex assembly, inducing nuclear pore complex disassembly, and inhibiting nuclear pore complex function by targeting different nuclear pore complex components triggers cell death of excessively proliferating cells in proliferative disease or disorder. In some instances, the proliferative disease is cancer. In some instances, the proliferative disease is atherosclerosis. In some instances, the proliferative disease is various forms of arthritis. In some instances, the proliferative disease is rheumatoid arthritis. In some instances, the proliferative disease is psoriasis. In some instances, the proliferative disease is various forms of fibrosis. In some instances, the proliferative disease is idiopathic pulmonary fibrosis. In some instances, the proliferative disease is scleroderma. In some instances, the proliferative disease is cirrhosis of the liver. In some instances, the proliferative disease is benign prostatic hyperplasia. In some instances, the proliferative disease is abnormal scar formation. In some instances, the proliferative disease is inflammatory bowel disease.

Nucleoporins

Nucleoporins are a family of proteins that are the constituent building blocks of the nuclear pore complex. Nucleoporins mediate transport of macromolecules between the cell nucleus and cytoplasm in eukaryotes. In some instances, certain nucleoporins form the structural scaffolding of the nuclear pore complex. In some instances, certain nucleoporins function by interacting with transport molecules known as karyopherins. There are three types of nucleoporins, namely structural nucleoporins, membrane nucleoporins, and FG-nucleoporins. Structural nucleoporins form the ring portion of the nuclear pore complex. They span the membrane of the nuclear envelope and are referred to as the scaffolding of the nuclear pore. Two sub-complexes of structural nucleoporins form the two scaffold rings of each nuclear pore. Membrane nucleoporins are localized to the curvature of a nuclear pore. These proteins are embedded within the nuclear membrane at the region where the inner and outer leaflets connect. FG-nucleoporins are so named because they contain repeats of the amino acid residues phenylalanine and glycine. FG-repeats are small hydrophobic segments that break up long stretches of hydrophilic amino acids. These FG-repeat segments are found in long random-coil portions of the protein which stretch into the channel of nuclear pores and are primarily responsible for the selective permeability of nuclear pore complexes. These segments of FG-nucleoporins form a mass of chains which allow smaller molecules to diffuse through, but exclude large hydrophilic macromolecules. These large molecules are only able to cross a nuclear pore if they are accompanied by a transport receptor molecule that temporarily interacts with a nucleoporin's FG-repeat segment. FG-nucleoporins also contain a globular portion that serves as an anchor for attachment to the nuclear pore complex.

The family of nucleoporins comprises of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS. Nucleoporins have been shown to form various sub-complexes with one another. The most common of these complexes or binding/interacting pairs are listed in Table 1.

TABLE 1

Nucleoporin protein binding or interacting pairs

| | | |
|---|---|---|
| Nup133-Nup160 | Nup358(RanBP2)-Nup188 | Nup35- Nup358(RanBP2) |
| Nup133-Nup107 | Nup358(RanBP2)-Nup93 | Nup50-Nup98 |
| Nup133-Nup37 | Nup358(RanBP2)-Nup160 | Nup50-Nup153 |
| Nup133-Nup43 | Nup358(RanBP2)-Seh1L | Nup153-Nup54 |
| Nup133-Nup50 | Nup358(RanBP2)-Sec13 | Nup153-Nup62 |
| Nup133-Nup153 | Nup93-Nup35 | Nup153-Nup88 |
| Nup133-Nup155 | Nup93-Nup62 | Nup153-Nup93 |
| Nup133-Nup214 | Nup93-Nup54 | Nup153-Nup98 |
| Nup133-Nup98 | Nup93-Nup58 | Nup153-Nup155 |
| Nup133-Sec13 | Nup93-Nup45 | Nup153-Nup205 |
| Nup133-Seh1L | Nup93-Nup98 | Nup153-Nup214 |
| Nup107-Nup96 | Nup93-Nup205 | Nup153-hCG1(Nup12) |
| Nup107-Nup50 | Nup93-Nup214 | ELYS-Nup37 |
| Nup107-Nup54 | Nup205-Nup155 | ELYS -Nup43 |
| Nup107-Nup62 | Nup205-Nup35 | ELYS -Nup75(Nup85) |
| Nup107-Nup88 | Nup205-Nup98 | ELYS -Nup96 |
| Nup107-Nup93 | Nup205-Nup188 | ELYS -Nup107 |
| Nup107-Nup98 | Nup205-Nup214 | ELYS -Nup133 |
| Nup107-Nup153 | Nup205-Nup358 | ELYS -Nup160 |
| Nup107-Nup155 | Nup205- hCG1(Nupl2) | ELYS -Sec13 |
| Nup107-Nup205 | Nup155-Nup35 | ELYS -Seh11 |
| Nup107-Nup214 | Nup155-Nup37 | ELYS-Nup35 |
| Nup107-Sec13 | Nup155-Nup62 | ELYS-Nup98 |
| Nup107-Seh1L | Nup155-Nup54 | Nup62-Nup54 |
| Nup96-Sec13 | Nup155- Nup58 | Nup62-Nup88 |
| Nup96-Nup75(Nup85) | Nup155- Nup45 | Nup62-Nup98 |
| Nup96-Seh1L | Nup155-Nup98 | Nup62-Nup188 |
| Nup96- Nup160 | Nup155-Nup214 | Nup62-Nup214 |
| Nup96-Nup37 | Nup98-Nup88 | Nup62-Nup358(RanBP2) |
| Nup96-Nup155 | Pom121-NDC1 | Nup98-Nup54 |

TABLE 1-continued

| Nucleoporin protein binding or interacting pairs | | |
|---|---|---|
| Nup160-Nup50 | Pom121-Nup35 | Nup98-Nup214 |
| Nup160-Nup37 | Pom121-Nup43 | Nup98-Nup358(RanBP2) |
| Nup160-Nup43 | Pom121-Nup75(Nup85) | TPR-Nup93 |
| Nup160-Nup107 | Pom121-Nup133 | TPR-Nup98 |
| Nup160-SehL1 | Pom121-Nup153 | TPR-Nup107 |
| Nup160-Sec13 | Pom121-Nup160 | TPR-Nup153 |
| Nup160-Nup153 | Pom121-Pom121 | TPR-Nup205 |
| Nup160-Nup155 | NDC 1-NDC1 | RAE1-Nup54 |
| Nup160-Nup214 | NDC1-Nup37 | RAE1-Nup62 |
| Nup160-Nup98 | NDC1-Nup43 | RAE1-Nup88 |
| Nup37-Sehl1 | NDC1-Nup75(Nup85) | RAE1-Nup93 |
| Nup37-Sec13 | NDC1-Nup96 | RAE1-Nup98 |
| Nup37-Nup358(RanBP2) | NDC1-Nup107 | RAE1-Nup107 |
| Nup37-Nup43 | NDC1-Nup133 | RAE1-Nup153 |
| Nup37-Nup75(Nup85) | NDC1-Nup160 | RAE1-Nup188 |
| Nup37-Nup98 | NDC1-Sec13 | RAE1-Nup214 |
| Nup37-Nup107 | NDC1-Sehl1 | RAE1-Nup358(RanBP2) |
| Nup37-Nup153 | NDC1-ELYS | RAE1-hCG1(Nupl2) |
| Nup43-Sehl1 | NDC1-Nup35 | GLE1-Nup35 |
| Nup43-Sec13 | NDC1-Nup93 | GLE1-Nup98 |
| Nup43-Nup50 | NDC1-Nup98 | GLE1-Nup107 |
| Nup43-Nup358(RanBP2) | NDC1-Nup153 | GLE1-Nup153 |
| Nup43-Nup75(Nup85) | NDC1-Nup155 | GLE1-Nup155 |
| Nup43-Nup98 | NDC1-Nup188 | GLE1-NupSeh1 |
| Nup43-Nup107 | NDC1-Nup205 | GLE1-Nup358(RanBP2) |
| Nup43-Nup153 | NDC1-Nup58 | GLE1-Nup58 |
| Nup43-Nup155 | NDC1-Nup358(RanBP2) | GLE1-ALADIN |
| Nup43-Nup214 | Nup58-Nup35 | ALADIN-NDC 1 |
| Nup75(Nup85)-Seh1L | Nup58-Nup54 | ALADIN-Nup35 |
| Nup75(Nup85)-Sec13 | Nup58-Nup62 | ALADIN-Nup98 |
| Nup75(Nup85)-Nup50 | Nup58-Nup98 | ALADIN-Nup107 |
| Nup75(Nup85)-Nup62 | Nup58-Nup107 | ALADIN-Nup153 |
| Nup75(Nup85)-Nup88 | Nup58-Nup188 | ALADIN-Nup358 |
| Nup75(Nup85)-Nup98 | Nup58-Nup205 | ALADIN-Seh1L |
| Nup75(Nup85)-Nup107 | Nup58-Nup214 | Nup210-Nup98 |
| Nup75(Nup85)-Nup153 | Nup58-hCG1(Nup12) | Nup210-Nup107 |
| Nup75(Nup85)-Nup155 | Nup58-Nup358(RanBP2) | Nup210-Nup153 |
| Nup75(Nup85)-Nup160 | hCG1(Nupl2)-Nup35 | Nup210-Nup214 |
| Nup75(Nup85)-Nup214 | hCG1(Nupl2)-Nup98 | Nup210-Seh1L |
| Sec13-Seh1 | hCG1(Nupl2)-Nup107 | Nup210-NDC1 |
| Sec13-Nup98 | hCG1(Nupl2)-Nup214 | Nup210-Pom121 |
| Sec13-Nup155 | hCG1(Nupl2)-Nup358(RanBP2) | Nup210-Nup210 |
| Seh1-Nup88 | Nup188-Nup35 | Nup210-Nup37 |
| Seh1-Nup93 | Nup188-Nup93 | Nup210-Nup43 |
| Seh1-Nup98 | Nup188-Nup98 | Nup210-Nup75(Nup85) |
| Seh1-Nup153 | Nup188-Nup107 | Nup210-Nup96 |
| Seh1-Nup155 | Nup188-Nup153 | Nup210-Nup107 |
| Seh1-Nup205 | Nup188-Nup214 | Nup210-Nup133 |
| Seh1-Nup214 | Nup188-Seh1L | Nup210-Nup160 |
| Seh1-Rae1 | Nup188-hCG1(Nup12) | Nup210-Nup35 |
| Nup214-Nup88 | Nup35-Nup50 | Nup210-Nup93 |
| Nup214-Nup358(RanBP2) | Nup35-Nup54 | Nup210-Nup155 |
| Nup88-Nup358(RanBP2) | Nup35-Nup62 | Nup210-Nup188 |
| Nup358(RanBP2)-Nup50 | Nup35-Nup88 | Nup210-Nup205 |
| Nup358(RanBP2)-Nup75(Nup85) | Nup35-Nup98 | Nup210-Seh1L |
| Nup358(RanBP2)-Nup107 | Nup35-Nup107 | Nup210-Sec13 |
| Nup358(RanBP2)-Nup133 | Nup35-Nup153 | Nup210-ELYS |
| Nup358(RanBP2)-Nup153 | Nup35-Nup214 | NDC1-Nup45 |
| Nup358(RanBP2)-Nup155 | Nup35-Seh1L | GLE1-Nup45 |
| Nup45-Nup35 | Nup133-Nup96 | Pom121-Sec13 |
| Nup45-Nup54 | Pom133-Nup75(Nup85) | Pom121-ELYS |
| Nup45-Nup62 | Nup133-Nup35 | Pom121-Nup93 |
| Nup45-Nup98 | Nup133-Nup93 | Pom121-Nup155 |
| Nup45-Nup107 | Nup133-Nup188 | Pom121-Nup188 |
| Nup45-Nup188 | Nup133-Nup205 | Pom121-Nup205 |
| Nup45-Nup205 | Nup107-Pom121 | Nup43-Nup96 |
| Nup45-Nup214 | Pom121-Nup96 | Nup43-Nup35 |
| Nup45-hCG1(Nupl2) | Pom121-Nup96 | Nup43-Nup93 |
| Nup45-Nup358(RanBP2) | Pom121-Seh1 | Nup43-Nup188 |
| Nup43-Nup205 | Nup188-Nup62 | Nup96-Nup205 |
| Nup93-Nup155 | Nup62-Nup62 | Nup160-Nup35 |
| Nup205-Nup54 | Nup96-Nup35 | Nup160-Nup93 |
| Nup205-Nup62 | Nup96-Nup93 | Nup160-Nup188 |
| Nup188-Nup54 | Nup96-Nup188 | Nup160-Nup205 |
| Sec13-Nup35 | Nup75(Nup85)-Nup35 | Nup37-Nup35 |
| Sec13-Nup93 | Nup75(Nup85)-Nup93 | Nup37-Nup93 |
| Sec13-Nup188 | Nup75(Nup85)-Nup188 | Nup37-Nup188 |
| Sec13-Nup205 | Nup75(Nup85)-Nup205 | Nup45-Nup45 |

TABLE 1-continued

Nucleoporin protein binding or interacting pairs

| | | |
|---|---|---|
| Nup155-Nup188 | Nup37-205 | Nup45-Nup58 |
| Nup54-Nup54 | Nup54-Nup58 | Nup58-Nup58 |

TABLE 2

Nucleoporin protein interacting pair candidates to disrupt NPC assembly

| | | |
|---|---|---|
| Nup133-Nup160 | Nup93-Nup35 | ELYS-Nup37 |
| Nup133-Nup107 | Nup93-Nup205 | ELYS -Nup43 |
| Nup133-Nup37 | Nup205-Nup155 | ELYS -Nup75(Nup85) |
| Nup133-Nup43 | Nup205-Nup35 | ELYS -Nup96 |
| Nup133-Nup155 | Nup205-Nup188 | ELYS -Nup160 |
| Nup133-Sec13 | Nup205-Nup214 | ELYS -Sec13 |
| Nup133-Seh1L | Nup155-Nup35 | ELYS -Seh1 |
| Nup133-Nup96 | Nup155-Nup37 | ELYS-Nup35 |
| Pom133-Nup75(Nup85) | Pom121-NDC1 | ELYS-Nup98 |
| Nup133-Nup35 | Pom121-Nup35 | Nup160-Nup37 |
| Nup133-Nup93 | Pom121-Nup43 | Nup160-Nup43 |
| Nup133-Nup188 | Pom121-Nup75(Nup85) | Nup160-SehL1 |
| Nup133-Nup205 | Pom121-Nup160 | Nup160-Sec13 |
| Pom121-Nup133 | Pom121-Pom121 | Nup160-Nup155 |
| ELYS -Nup133 | Pom121-Nup96 | Pom121-Nup205 |
| NDC1-Nup133 | Pom121-Nup96 | Nup37-205 |
| Nup107-Nup205 | Pom121-Seh1 | Nup37-Nup35 |
| Nup107-Sec13 | Pom121-Sec13 | Nup37-Nup93 |
| Nup107-Seh1L | Pom121-ELYS | Nup37-Nup188 |
| Nup107-Nup96 | Pom121-Nup93 | Nup37-Sehl1 |
| Nup107-Nup93 | Pom121-Nup155 | Nup37-Sec13 |
| Nup37-Nup107 | Pom121-Nup188 | Nup37-Nup43 |
| ELYS -Nup107 | NDC1-Nup160 | Nup37-Nup75(Nup85) |
| NDC1-Nup107 | NDC1-Sec13 | Nup43-Sehl1 |
| Nup160-Nup107 | NDC1-Sehl1 | Nup43-Sec13 |
| Nup43-Nup107 | NDC1-ELYS | Nup43-Nup75(Nup85) |
| Nup35-Nup107 | NDC1-Nup35 | Nup43-Nup155 |
| Nup188-Nup107 | NDC1-Nup93 | Nup43-Nup96 |
| Nup75(Nup85)-Nup107 | NDC1-Nup155 | Nup43-Nup35 |
| Nup107-Nup155 | NDC1-Nup188 | Nup43-Nup93 |
| Nup107-Pom121 | NDC1-Nup205 | Nup43-Nup188 |
| Sec13-Seh1 | NDC1-NDC1 | Nup43-Nup205 |
| Sec13-Nup155 | NDC1-Nup37 | Nup188-Nup35 |
| Seh1-Nup93 | NDC1-Nup43 | Nup188-Nup93 |
| Seh1-Nup155 | NDC1-Nup75(Nup85) | Nup188-Seh1L |
| Seh1-Nup205 | NDC1-Nup96 | Nup35-Seh1L |
| Nup75(Nup85)-Seh1L | Sec13-Nup35 | Nup160-Nup35 |
| Nup75(Nup85)-Sec13 | Sec13-Nup93 | Nup160-Nup93 |
| Nup75(Nup85)-Nup155 | Sec13-Nup188 | Nup160-Nup188 |
| Nup75(Nup85)-Nup160 | Sec13-Nup205 | Nup160-Nup205 |
| Nup96-Nup75(Nup85) | Nup93-Nup155 | Nup96-Sec13 |
| Nup75(Nup85)-Nup35 | Nup155-Nup188 | Nup96-Seh1L |
| Nup75(Nup85)-Nup93 | Nup96- Nup160 | Nup96-Nup35 |
| Nup75(Nup85)-Nup188 | Nup96-Nup37 | Nup96-Nup93 |
| Nup75(Nup85)-Nup205 | Nup96-Nup155 | Nup96-Nup188 |
| Nup96-Nup205 | | |

TABLE 3

Nucleoporin protein interacting pair candidates to disrupt NPC assembly or function

| | | |
|---|---|---|
| Nup35-Nup45 | Nup45-Nup45 | Nup62-Nup45 |
| Nup35-Nup54 | Nup45-Nup54 | Nup62-Nup54 |
| Nup35-Nup58 | Nup45-Nup58 | Nup62-Nup58 |
| Nup35-Nup62 | Nup54-Nup54 | Nup62-Nup62 |
| Nup93-Nup45 | Nup54-Nup58 | Nup205-Nup45 |
| Nup93-Nup54 | Nup58-Nup58 | Nup205-Nup54 |
| Nup93-Nup58 | Nup188-Nup45 | Nup205-Nup58 |
| Nup93-Nup62 | Nup188-Nup54 | Nup205-Nup62 |
| Nup155-Nup45 | Nup188-Nup58 | Nup155-Nup58 |
| Nup155-Nup54 | Nup188-Nup62 | Nup155-Nup62 |

Disclosed herein, in some embodiments, is a method for treating a proliferative disease or disorder in an individual in need thereof, comprising: administering to the individual a therapeutically effective amount of an agent that inhibits nuclear pore complex assembly, induces nuclear pore complex disassembly, or inhibits nuclear pore complex function. A pharmaceutical composition comprising an effective amount of such an agent of interest and a pharmaceutically acceptable excipient is also encompassed by the disclosure.

Exemplary Agents

Disclosed herein, in some embodiments, are agents that inhibit nuclear pore complex assembly, induce nuclear pore complex disassembly, or inhibit nuclear pore complex function. In some instances, the agent is a small molecule. In some instances, the agent is a small interfering RNA (siRNA). In some instances, the agent is a short hairpin RNA (shRNA). In some instances, the agent is a microRNA (miRNA). In some instances, the agent is a messenger RNA (mRNA). In some instances, the agent is a guideRNA (gRNA). In some instances, the agent is an antisense oligonucleotide. In some instances, the agent is a peptide. In some instances, the agent is a peptidomimetic. In some instances, the agent is an aptamer.

Small Molecule

Small molecule is a molecule that binds to a specific biological target—such as a specific protein or nucleic acid—and acts as an effector, altering the activity or function of the target. In some embodiments, disclosed herein, the methods comprise an agent that inhibits nuclear pore complex assembly, induces nuclear pore complex disassembly, or inhibits nuclear pore complex function. In some instances, the agent is a small molecule. In some instances, the small molecule binds to the nucleic acid or protein including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the small molecule disrupts a protein binding/interacting pair comprising pairs listed in Table 1. In some instances, the small molecule disrupts a protein binding/interacting pair comprising pairs listed in Table 2. In some instances, the small molecule disrupts a protein binding/interacting pair comprising pairs listed in Table 3. In some instances, the small molecule reduces synthesis of a protein, thereby inhibiting nuclear pore complex assembly, inducing nuclear pore complex disassembly, or inhibiting nuclear pore complex function.

Small Interfering RNA (siRNA)

Small interfering RNA (siRNA), sometimes known as short interfering RNA or silencing RNA, is a class of double-stranded RNA molecules, 20-25 base pairs in length, similar to miRNA, and operates within the RNA interference (RNAi) pathway. It interferes with the expression of specific genes with complementary nucleotide sequences by degrading mRNA after transcription, resulting in no translation. In some embodiments, disclosed herein, the methods comprise an agent that inhibits nuclear pore complex assembly, induces nuclear pore complex disassembly, or inhibits nuclear pore complex function. In some instances, the agent is a small interfering RNA (siRNA). In some instances, the siRNA has a sequence complementary to the target sequence of a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS. In some instances, the siRNA reduces synthesis of a protein, thereby inhibiting nuclear pore complex assembly, inducing nuclear pore complex disassembly, or inhibiting nuclear pore complex function.

Short Hairpin RNA (shRNA)

Short hairpin RNA (shRNA) or small hairpin RNA (shRNA/Hairpin Vector) is an artificial RNA molecule with a tight hairpin turn that is used to silence target gene expression via RNA interference (RNAi). Expression of shRNA in cells is typically accomplished by delivery of plasmids or through viral or bacterial vectors. Once the vector has integrated into the host genome, the shRNA is then transcribed in the nucleus and the product mimics pri-microRNA (pri-miRNA) and is processed by Drosha. The resulting pre-shRNA is exported from the nucleus and processed by Dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing. In some embodiments, disclosed herein, the methods comprise an agent that inhibits nuclear pore complex assembly, induces nuclear pore complex disassembly, or inhibits nuclear pore complex function. In some instances, the agent is a short hairpin RNA (shRNA). In some instances, the shRNA targets a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS. In some instances, the shRNA reduces synthesis of a protein, thereby inhibiting nuclear pore complex assembly, inducing nuclear pore complex disassembly, or inhibiting nuclear pore complex function.

MicroRNA (miRNA)

MicroRNA (miRNA) is a small non-coding RNA molecule (containing about 22 nucleotides) found in plants, animals and some viruses that functions in RNA silencing and post-transcriptional regulation of gene expression. Encoded by eukaryotic nuclear DNA in plants and animals and by viral DNA in certain viruses whose genome is based on DNA, miRNAs function via base-pairing with complementary sequences within mRNA molecules. As a result, these mRNA molecules are silenced, by one or more of the following processes: cleavage of the mRNA strand into two pieces, destabilization of the mRNA through shortening of its poly(A) tail, and less efficient translation of the mRNA into proteins by ribosomes. In some embodiments, disclosed herein, the methods comprise an agent that inhibits nuclear pore complex assembly, induces nuclear pore complex disassembly, or inhibits nuclear pore complex function. In some instances, the agent is a microRNA (miRNA). In some instances, the agent is a microRNA mimic. miRNA mimics contain non-natural or artificial double stranded miRNA-like RNA fragments. These RNA fragments are constructed to contain a sequence motif on its 5'-end that is partially complementary to the target sequence in the 3'UTR. Once these RNA fragments are introduced into cells the miRNA mimics binds specifically to the targeted gene. The result is posttranscriptional repression or translational inhibition of the gene. In some instances, the miRNA or miRNA mimic targets a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS. In some instances, the miRNA or miRNA mimic reduces synthesis of a protein, thereby inhibiting nuclear pore complex assembly, inducing nuclear pore complex disassembly, or inhibiting nuclear pore complex function.

Messenger RNA (mRNA)

Messenger RNA (mRNA) is a large family of RNA molecules that convey genetic information from DNA to the ribosome, where they specify the amino acid sequence of the protein products of gene expression. Following transcription of primary transcript mRNA (known as pre-mRNA) by RNA polymerase, processed, mature mRNA is translated into a polymer of amino acids: a protein. As in DNA, mRNA genetic information is in the sequence of nucleotides, which are arranged into codons consisting of three base pairs each. Each codon encodes for a specific amino acid, except the stop codons, which terminate protein synthesis. In some embodiments, disclosed herein, the methods comprise an agent that inhibits nuclear pore complex assembly, induces nuclear pore complex disassembly, or inhibits nuclear pore complex function. In some instances, the agent is a messenger RNA (mRNA). In some instances, the mRNA has a mutated binding domain of a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS, wherein the binding domain is non-functional but acts as a wild type, thereby outcompeting the wildtype mRNA and preventing structural function. In some instances, the mRNA has a mutated binding domain of a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS, wherein the binding domain is non-functional but acts as a wild type, thereby outcompeting the wildtype mRNA and preventing the transport of the component to the nuclear pore complex. In some instances, the mRNA has a mutated regulatory domain of a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS, wherein the regulatory domain is non-functional but acts as a wild type, thereby outcompeting the wildtype mRNA and preventing structural function. In some instances, the mRNA has a mutated regulatory domain of a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS, wherein the regulatory domain is non-functional but acts as a wild type, thereby outcompeting the wildtype mRNA and preventing the transport of the component to the nuclear pore complex. In some instances, the mRNA outcompetes the wildtype mRNA of a protein of the protein binding/interacting pairs listed in Table 1, thereby disrupting the pair. In some instances, the mRNA outcompetes the wildtype mRNA of a protein of the protein binding/interacting pairs listed in Table 2, thereby disrupting the pair. In some instances, the mRNA outcompetes the wildtype mRNA of a protein of the protein binding/interacting pairs listed in Table 3, thereby disrupting the pair. In some instances, the mRNA reduces synthesis of a protein, thereby inhibiting nuclear pore complex assembly, inducing nuclear pore complex disassembly, or inhibiting nuclear pore complex function.

GuideRNA (gRNA)

GuideRNA (gRNA) is a short synthetic RNA composed of a "scaffold" sequence necessary for Cas9-binding and a ~20 nucleotide "spacer" or "targeting" sequence which defines the genomic target to be modified. CRISPR was originally employed to "knock-out" target genes in various cell types and organisms, but modifications to the Cas9 enzyme have extended the application of CRISPR to selectively activate or repress target genes, purify specific regions of DNA, and even image DNA in live cells using fluorescence microscopy. In some embodiments, disclosed herein, the methods comprise an agent that inhibits nuclear pore complex assembly, induces nuclear pore complex disassembly, or inhibits nuclear pore complex function. In some instances, the agent is a guideRNA (gRNA). In some instances, the gRNA targets a nuclear pore complex component including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS. In some instances, the gRNA reduces synthesis of a protein, thereby inhibiting nuclear pore complex assembly, inducing nuclear pore complex disassembly, or inhibiting nuclear pore complex function.

Methods of Use

Disclosed herein, in some embodiments, is a method for treating a proliferative disease or disorder in an individual in need thereof, comprising: administering to the individual a therapeutically effective amount of an agent that inhibits nuclear pore complex assembly, induces nuclear pore complex disassembly, or inhibits nuclear pore complex function. Further disclosed, in some embodiments, are pharmaceutical composition, comprising (a) an agent that inhibits nuclear pore complex assembly, induces nuclear pore complex disassembly, or inhibits nuclear pore complex function; and (b) a pharmaceutically acceptable excipient.

In some instances, the agent inhibits expression of a component of the nuclear pore complex. In some instances, the agent promotes degradation of a component of the nuclear pore complex. In some instances, the agent inhibits function of a component of the nuclear pore complex. In some instances, the agent modulates the expression of a regulator of the nuclear pore complex assembly. In some instances, the agent inhibits expression of a regulator of the nuclear pore complex assembly. In some instances, the agent modulates the function of a regulator of the nuclear pore complex assembly. In some instances, the agent inhibits function of a regulator of the nuclear pore complex assembly. In some instances, the agent modulates the expression of a regulator of the nuclear pore complex disassembly. In some instances, the agent modulates the function of a regulator of the nuclear pore complex disassembly. In some instances, the agent inhibits interaction between the components of nuclear pore complex. In some instances, the agent inhibits the recruitment of nucleoporins to the nuclear pore complex. In some instances, the agent inhibits the assembly of structure intermediates or pre-pores of nuclear pore complex. In some instances, the agent inhibits cell proliferation in malignant cells. In some instances, the agent inhibits cell proliferation in abnormally proliferative cells. In some instances, the agent induces cell death in malignant cells. In some instances, the agent induces cell death in abnormally proliferative cells.

In some instances, the agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1 (Nup12), Aladin, TPR, GLE1, and ELYS of the nuclear pore complex. In some instances, the agent inhibits Nup35 of the nuclear pore complex. In some instances, the agent inhibits Nup37 of the nuclear pore complex. In some instances, the agent inhibits Nup43 of the nuclear pore complex. In some instances, the agent inhibits Nup45 of the nuclear pore complex. In some instances, the agent inhibits Nup50 of the nuclear pore complex. In some instances, the agent inhibits Nup54 of the nuclear pore complex. In some instances, the agent inhibits Nup58(Nup11) of the nuclear pore complex. In some instances, the agent inhibits Nup62 of the nuclear pore complex. In some instances, the agent inhibits Nup75/85 of the nuclear pore complex. In some instances, the agent inhibits Nup93 of the nuclear pore complex. In some instances, the agent inhibits Nup96 of the nuclear pore complex. In some instances, the agent inhibits Nup107 of the nuclear pore complex. In some instances, the agent inhibits Nup133 of the nuclear pore complex. In some instances, the agent inhibits Nup155 of the nuclear pore complex. In some instances, the agent inhibits Nup160 of the nuclear pore complex. In some instances, the agent inhibits Nup358(RanBP2) of the nuclear pore complex. In some instances, the agent inhibits Seh1 of the nuclear pore complex. In some instances, the agent inhibits Sec13 of the nuclear pore complex. In some instances, the agent inhibits NDC1 of the nuclear pore complex. In some instances, the agent inhibits Pom121 of the nuclear pore complex. In some instances, the agent Nup210 of the nuclear pore complex. In some instances, the agent inhibits RAE1 of the nuclear pore complex. In some instances, the agent inhibits HCG1/CG1 (Nup12) of the nuclear pore complex. In some instances, the agent inhibits Aladin of the nuclear pore complex. In some instances, the agent inhibits TPR of the nuclear pore complex. In some instances, the agent inhibits GLE1 of the nuclear pore complex. In some instances, the agent inhibits ELYS of the nuclear pore complex. In some instances, the agent inhibits a component of the nuclear pore complex comprising a protein binding pair, thereby disrupting the pair. In some instances, the protein binding/interacting pair is selected from a pair listed in Table 1. In some instances, the protein binding/interacting pair is selected from a pair listed in Table 2. In some instances, the protein binding/interacting pair is selected from a pair listed in Table 3.

In some instances, the agent is a small molecule. In some instances, the agent is a small interfering RNA (siRNA). In some instances, the agent is a short hairpin RNA (shRNA). In some instances, the agent is a microRNA (miRNA). In some instances, the agent is a messenger RNA (mRNA). In some instances, the agent is a guideRNA (gRNA).

In some instances, the method further comprises administering an additional therapeutic agent. In some instances, the agent and the additional therapeutic agent are administered simultaneously. In some instances, the agent and the additional therapeutic agent are administered sequentially. In some instances, the agent is administered before administering the additional therapeutic agent. In some instances, the agent is administered after administering the additional therapeutic agent. In some instances, the additional therapeutic agent is an anti-proliferative agent. In some instances, the additional therapeutic agent is anti-cancer agent. In some instances, the additional therapeutic agent is a chemotherapeutic agent. In some instances, the additional therapeutic agent is a hormonal agent. In some instances, the additional therapeutic agent is an anti-inflammatory agent. In some instances, the additional therapeutic agent is a steroid. In some instances, the additional therapeutic agent is an immunotherapeutic agent. In some instances, the additional therapeutic agent is a targeted therapy agent.

In some instances, the agent and the additional therapeutic agent are administered continuously for 1, 2, 3, 4, 5, 6, 7, 8, 9, 10, 14, 15, 28, 30 or more days. In some instances, the agent and the additional therapeutic agent are administered continuously for 1 or more days. In some instances, the agent and the additional therapeutic agent are administered continuously for 2 or more days. In some instances, the agent and the additional therapeutic agent are administered continuously for 3 or more days. In some instances, the agent and the additional therapeutic agent are administered continuously for 4 or more days. In some instances, the agent and the additional therapeutic agent are administered continuously for 5 or more days. In some instances, the agent and the additional therapeutic agent are administered continuously for 6 or more days. In some instances, the agent and the additional therapeutic agent are administered continuously for 7 or more days. In some instances, the agent and the additional therapeutic agent are administered continuously for 8 or more days. In some instances, the agent and the additional therapeutic agent are administered continuously for 9 or more days. In some instances, the agent and the additional therapeutic agent are administered continuously for 10 or more days. In some instances, the agent and the additional therapeutic agent are administered continuously for 14 or more days. In some instances, the agent and the additional therapeutic agent are administered continuously for 15 or more days. In some instances, the agent and the additional therapeutic agent are administered continuously for 28 or more days. In some instances, the agent and the additional therapeutic agent are administered continuously for 30 or more days.

In some cases, the agent and the additional therapeutic agent are administered at predetermined time intervals for 1, 2, 3, 4, 5, 6, 7, 8, 9, 10, 14, 15, 28, 30 or more days. In some instances, the agent and the additional therapeutic agent are administered at predetermined time intervals for 1 or more days. In some instances, the agent and the additional therapeutic agent are administered at predetermined time intervals for 2 or more days. In some instances, the agent and the additional therapeutic agent are administered at predetermined time intervals for 3 or more days. In some instances, the agent and the additional therapeutic agent are administered at predetermined time intervals for 4 or more days. In some instances, the agent and the additional therapeutic agent are administered at predetermined time intervals for 5 or more days. In some instances, the agent and the additional therapeutic agent are administered at predetermined time intervals for 6 or more days. In some instances, the agent and the additional therapeutic agent are administered at predetermined time intervals for 7 or more days. In some instances, the agent and the additional therapeutic agent are administered at predetermined time intervals for 8 or more days. In some instances the agent and the additional therapeutic agent are administered at predetermined time intervals for 9 or more days. In some instances, the agent and the additional therapeutic agent are administered at predetermined time intervals for 10 or more days. In some instances, the agent and the additional therapeutic agent are administered at predetermined time intervals for 14 or more days. In some instances, the agent and the additional therapeutic agent are administered at predetermined time intervals for 15 or more days. In some instances, the agent and the additional therapeutic agent are administered at predetermined time intervals for 28 or more days. In some instances, the agent and the additional therapeutic agent are administered at predetermined time intervals for 30 or more days.

In some embodiments, the agent and the additional therapeutic agent are administered at predetermined time intervals for 1, 2, 3, 4, 5, 6, 7, 8, 9, 10, 11, 12, 24, 36 or more months. In some instances, the agent and the additional therapeutic agent are administered at predetermined time intervals for 1 or more month. In some instances, the agent and the additional therapeutic agent are administered at predetermined time intervals for 2 or more months. In some instances the agent and the additional therapeutic agent are administered at predetermined time intervals for 3 or more months. In some instances, the agent and the additional therapeutic agent are administered at predetermined time intervals for 4 or more months. In some instances, the agent and the additional therapeutic agent are administered at predetermined time intervals for 5 or more months. In some instances, the agent and the additional therapeutic agent are administered at predetermined time intervals for 6 or more months. In some instances, the agent and the additional therapeutic agent are administered at predetermined time intervals for 7 or more months. In some instances, the agent and the additional therapeutic agent are administered at predetermined time intervals for 8 or more months. In some instances, the agent and the additional therapeutic agent are administered at predetermined time intervals for 9 or more months. In some instances, the agent and the additional therapeutic agent are administered at predetermined time intervals for 10 or more months. In some instances, the agent and the additional therapeutic agent are administered at predetermined time intervals for 11 or more months. In some instances, the agent and the additional therapeutic agent are administered at predetermined time intervals for 12 or more months. In some instances, the agent and the additional therapeutic agent are administered at predetermined time intervals for 24 or more months. In some instances, the agent and the additional therapeutic agent are administered at predetermined time intervals for 36 or more months.

In some cases, the agent and the additional therapeutic agent are administered intermittently for 1, 2, 3, 4, 5, 6, 7, 8, 9, 10, 14, 15, 28, 30 or more days. In some instances, the agent and the additional therapeutic agent are administered intermittently for 1 or more days. In some instances, the agent and the additional therapeutic agent are intermittently for 2 or more days. In some instances the agent and the additional therapeutic agent are administered intermittently for 3 or more days. In some instances, the agent and the additional therapeutic agent are administered intermittently for 4 or more days. In some instances, the agent and the additional therapeutic agent are administered intermittently for 5 or more days. In some instances, the agent and the additional therapeutic agent are administered intermittently for 6 or more days. In some instances, the agent and the additional therapeutic agent are administered intermittently for 7 or more days. In some instances, the agent and the additional therapeutic agent are administered intermittently for 8 or more days. In some instances, the agent and the additional therapeutic agent are administered intermittently for 9 or more days. In some instances, the agent and the additional therapeutic agent are administered intermittently for 10 or more days. In some instances, the agent and the additional therapeutic agent are administered intermittently for 14 or more days. In some instances, the agent and the additional therapeutic agent are administered intermittently for 15 or more days. In some instances, the agent and the additional therapeutic agent are administered intermittently for 28 or more days. In some instances, the agent and the additional therapeutic agent are administered intermittently for 30 or more days.

In some instances, the agent is administered to an individual at a therapeutically effective amount. For example, the therapeutically effective amount is optionally administered in 1 dose, 2 doses, 3 doses, 4 doses, 5 doses, 6 doses or more. In some instances, the therapeutically effective amount of an agent is administered to an individual in 1 dose. In some instances, the therapeutically effective amount of an agent is administered to an individual in 2 or more doses. In some instances, the therapeutically effective amount of an agent is administered an individual in 3 or more doses. In some instances, the therapeutically effective amount of an agent is administered an individual in 4 or more doses. In some instances, the therapeutically effective amount of an agent is administered to an individual in 5 or more doses. In some instances, the therapeutically effective amount of an agent is administered an individual in 6 or more doses.

In some instances, the disease or disorder has abnormal nuclear transport. In some instances, the disease or disorder has normal nuclear transport. In some instances, the disease or disorder is a neoplastic disease. In some instances, the disease or disorder is caused by a malignant cell. In some instances, the disease or disorder is an inflammatory disease. In some instances, the disease or disorder is cancer. In some instances, the cancer has a mutation in the Ras gene. In some instances, the mutation is a G12D mutation. In some instances, the proliferative disease is atherosclerosis. In some instances, the proliferative disease is various forms of arthritis. In some instances, the proliferative disease is rheumatoid arthritis. In some instances, the proliferative disease is psoriasis. In some instances, the proliferative disease is various forms of fibrosis. In some instances, the proliferative disease is idiopathic pulmonary fibrosis. In some instances, the proliferative disease is scleroderma. In some instances, the proliferative disease is cirrhosis of the liver. In some instances, the proliferative disease is benign prostatic hyperplasia. In some instances, the proliferative disease is abnormal scar formation. In some instances, the proliferative disease is inflammatory bowel disease.

Additional Therapeutic Agents

In some embodiments, one or more methods described herein further comprising administering an additional therapeutic agent. In some embodiments, the additional therapeutic agent comprises an anti-proliferative agent, chemotherapeutic agent, a hormonal agent, a cytotoxin, a steroid, an immunotherapeutic agent, a targeted therapy agent, or an anti-inflammatory agent.

Chemotherapies as additional therapeutic agents include, but are not limited to, hormone modulators, androgen receptor binding agents (e.g., anti-androgens, bicalutamide, flutamide, nilutamide, MDV3100), gonadotropin-releasing hormone agonists and antagonists (e.g., leuprolide, buserelin, histrelin, goserelin, deslorelin, nafarelin, abarelix, cetrorelix, ganirelix degarelix), androgen synthesis inhibitors (abiraterone, TOK-001), temozolomide, mitozolomide, dacarbazine, cisplatin (CDDP), carboplatin, procarbazine, mechlorethamine, cyclophosphamide, camptothecin, ifosfamide, melphalan, chlorambucil, busulfan, nitrosurea, dactinomycin, anthracyclines (e.g., daunorubicin, doxorubicin, epirubicin, idarubicin), bleomycin, plicomycin, mitomycin, etoposide (VP16), tamoxifen, raloxifene, estrogen receptor binding agents, cabazitaxel, paclitaxel, gemcitabine, navelbine, farnesyl-protein transferase inhibitors, transplatinum, 5-fluorouracil, capecitabine, vincristin, vinblastin and methotrexate, topoisomerase inhibitors (e.g., irinotecan, topotecan, camptothecin, etoposide) or any derivative related agent of the foregoing. Many of the above agents are also referred to as hormone therapy agents such as, for example, androgen receptor binding agents, gonadotropin-releasing hormone agonists and antagonists, androgen synthesis inhibitors, estrogen receptor binding agents as well as aromatase inhibitors.

Immunotherapeutic agents generally rely on the use of immune effector cells and molecules to target and destroy cancer cells. The immune effector may be, for example, a tumor antigen or an antibody specific for some marker on the surface of a tumor cell. The tumor antigen or antibody alone may serve as an effector of therapy or it may recruit other cells to actually effect cell killing. An antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. Alternatively, a tumor antigen may stimulate a subject's immune system to target the specific tumor cells using cytotoxic T cells and NK cells. Immunotherapies include cancer vaccines such as Sipuleucel-T, tumor-targeting antibodies such as bevacizumab and trastuzumab, T cell engagers, adoptive cell therapies and the like.

Pharmaceutical Composition and Formulations

Disclosed herein, in some embodiments, are pharmaceutical composition, comprising (a) an agent that inhibits nuclear pore complex assembly, induces nuclear pore complex disassembly, or inhibits nuclear pore complex function; and (b) a pharmaceutically acceptable excipient.

In certain embodiments, disclosed herein include pharmaceutical compositions and formulations comprising an agent described herein. In some embodiments, the pharmaceutical compositions described herein are formulated for administering to a subject by systemic administration. In other embodiments, the pharmaceutical compositions described herein are formulated for administering to a subject by local administration. In some instances, the administration routes include, but are not limited to, parenteral (e.g., intravenous, subcutaneous, intramuscular, intracerebral, intracerebroventricular, intra-articular, intraperitoneal, or intracranial), oral, sublingual, intranasal, buccal, rectal, or transdermal administration routes. In some instances, the pharmaceutical composition describe herein is formulated for parenteral (e.g., intravenous, subcutaneous, intramuscular, intracerebral, intracerebroventricular, intra-articular, intraperitoneal, or intracranial) administration. In other instances, the pharmaceutical composition describe herein is formulated for oral administration. In additional instances, the pharmaceutical composition describe herein is formulated for sublingual administration. In additional instances, the pharmaceutical composition describe herein is formulated for intranasal administration. In some cases, the pharmaceutical composition is administered to a subject as an injection. In other instances, the pharmaceutical composition is administered to a subject as an infusion.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug* Delivery Systems, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Paces® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof. Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens for a Pharmaceutical Composition

In some embodiments, a pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Screening for Agents

Disclosed herein, in some embodiments, are methods of screening for a therapeutic agent for treating a proliferative disease or disorder in an individual in need thereof, the method comprising: (a) contacting a cell with a test agent; (b) detecting (i) inhibition of nuclear pore complex assembly as compared to a control; or (ii) induction of nuclear pore complex disassembly as compared to a control; and (c) identifying the test agent as a therapeutic agent if the test agent reduces the number of nuclear pore complexes in the cell as compared to the control.

In some instances, the cell is a tumor cell in vitro. In some instances, the cell is a tumor cell in vivo. In some instances, step (b) comprises performing: (i) cell proliferation or survival assay in vitro; and (ii) tumor formation, growth or metastasis assay in vivo.

In some instances, the in vivo assay is a Protein-fragment complementation assay, or PCA. In some instances, the in vivo assay is a Bimolecular Fluorescence Complementation (BiFC) assay. In some instances, the in vivo assay is a Fluorescence resonance energy transfer (FRET) assay.

In some instances, the detection is by direct visualization. In some instances, the detection is by microscopy imaging, Western blot, immunohistochemistry, ELISA, SPARCL, fluorescent signal detector, chromatography, radioactive binding assay, a fluorescence binding assay, a kinetic exclusion assay, a crystallography assay, or live imaging.

In some instances, the agent inhibits expression of a component of the nuclear pore complex. In some instances, the agent promotes degradation of a component of the nuclear pore complex. In some instances, the agent inhibits function of a component of the nuclear pore complex. In some instances, the agent modulates the expression of a regulator of the nuclear pore complex assembly. In some instances, the agent inhibits expression of a regulator of the nuclear pore complex assembly. In some instances, the agent modulates the function of a regulator of the nuclear pore complex assembly. In some instances, the agent inhibits function of a regulator of the nuclear pore complex assembly. In some instances, the agent modulates the expression of a regulator of the nuclear pore complex disassembly. In some instances, the agent modulates the function of a regulator of the nuclear pore complex disassembly. In some instances, the agent inhibits interaction between the components of nuclear pore complex. In some instances, the agent disrupts a protein binding/interacting pair comprising pairs listed in Table 1. In some instances, the agent disrupts a protein binding/interacting pair comprising pairs listed in Table 2. In some instances, the agent disrupts a protein binding/interacting pair comprising pairs listed in Table 3. In some instances, the agent inhibits synthesis of a component of the nuclear pore complex, thereby inhibiting nuclear pore complex assembly, inducing nuclear pore complex disassembly, or inhibiting nuclear pore complex function. In some instances, the agent disrupts the transport of the nucleoporins. In some instances, the agent inhibits the recruitment of nucleoporins to the nuclear pore complex. In some instances, the agent inhibits the assembly of structure intermediates or pre-pores of nuclear pore complex. In some instances, the agent inhibits cell proliferation in malignant cells. In some instances, the agent inhibits cell proliferation in abnormally proliferative cells. In some instances, the agent induces cell death in malignant cells. In some instances, the agent induces cell death in abnormally proliferative cells.

In some instances, the agent inhibits expression or function of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits Nup35 of the nuclear pore complex. In some instances, the agent inhibits Nup37 of the nuclear pore complex. In some instances, the agent inhibits Nup43 of the nuclear pore complex. In some instances, the agent inhibits Nup45 of the nuclear pore complex. In some instances, the agent inhibits Nup50 of the nuclear pore complex. In some instances, the agent inhibits Nup54 of the nuclear pore complex. In some instances, the agent inhibits Nup58(Nup11) of the nuclear pore complex. In some instances, the agent inhibits Nup62 of the nuclear pore complex. In some instances, the agent inhibits Nup75/85 of the nuclear pore complex. In some instances, the agent inhibits Nup93 of the nuclear pore complex. In some instances, the agent inhibits Nup96 of the nuclear pore complex. In some instances, the agent inhibits Nup107 of the nuclear pore complex. In some instances, the agent inhibits Nup133 of the nuclear pore complex. In some instances, the agent inhibits Nup155 of the nuclear pore complex. In some instances, the agent inhibits Nup160 of the nuclear pore complex. In some instances, the agent inhibits Nup358(RanBP2) of the nuclear pore complex. In some instances, the agent inhibits Seh1 of the nuclear pore complex. In some instances, the agent inhibits Sec13 of the nuclear pore complex. In some instances, the agent inhibits NDC1 of the nuclear pore complex. In some instances, the agent inhibits Pom121 of the nuclear pore complex. In some instances, the agent Nup210 of the nuclear pore complex. In some instances, the agent inhibits RAE1 of the nuclear pore complex. In some instances, the agent inhibits HCG1/CG1 (Nup12) of the nuclear pore complex. In some instances, the agent inhibits Aladin of the nuclear pore complex. In some instances, the agent inhibits TPR of the nuclear pore complex. In some instances, the agent inhibits GLE1 of the nuclear pore complex. In some instances, the agent inhibits ELYS of the nuclear pore complex. In some instances, the agent inhibits binding of a component of the nuclear pore complex to other components of the nuclear pore complex. In some instances, the agent inhibits a component of the nuclear pore complex comprising a protein binding pair, thereby disrupting the pair. In some instances, the protein binding pair is selected from a pair listed in Table 1. In some instances, the protein binding pair is selected from a pair listed in Table 2. In some instances, the protein binding pair is selected from a pair listed in Table 3. In some instances, the therapeutic agent targets the RNA or DNA of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent binds to Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex.

In some instances, the therapeutic agent is a small molecule. In some instances, the therapeutic agent is a small interfering RNA (siRNA). In some instances, the therapeutic agent is a short hairpin RNA (shRNA). In some instances, the therapeutic agent is a microRNA (miRNA). In some instances, the therapeutic agent is a messenger RNA (mRNA). In some instances, the therapeutic agent is a guideRNA (gRNA). In some instances, the therapeutic agent is an antisense oligonucleotide. In some instances, the therapeutic agent is a peptide. In some instances, the therapeutic agent is a peptidomimetic. In some instances, the therapeutic agent is an aptamer.

In some instances, the disease or disorder has abnormal nuclear transport. In some instances, the disease or disorder has normal nuclear transport. In some instances, the disease or disorder is a neoplastic disease. In some instances, the disease or disorder is caused by a malignant cell. In some instances, the disease or disorder is an inflammatory disease. In some instances, the disease or disorder is cancer. In some instances, the cancer has a mutation in the Ras gene. In some instances, the mutation is a G12D mutation. In some instances, cancer with G12D mutation is more sensitive to the agent. In some instances, the proliferative disease is atherosclerosis. In some instances, the proliferative disease is various forms of arthritis. In some instances, the proliferative disease is rheumatoid arthritis. In some instances, the proliferative disease is psoriasis. In some instances, the proliferative disease is various forms of fibrosis. In some instances, the proliferative disease is idiopathic pulmonary fibrosis. In some instances, the proliferative disease is scleroderma. In some instances, the proliferative disease is cirrhosis of the liver. In some instances, the proliferative disease is benign prostatic hyperplasia. In some instances, the proliferative disease is abnormal scar formation. In some instances, the proliferative disease is inflammatory bowel disease.

Disclosed herein, in some embodiments, are methods of screening for a therapeutic agent for treating a proliferative disease or disorder in an individual in need thereof, the method comprising: (a) contacting a cell with a test agent; (b) detecting inhibition of nuclear transport as compared to a control; and (c) identifying the test agent as a therapeutic agent if the test agent reduces the expression or activity of a component of nuclear pore complex in the cell as compared to the control.

In some instances, the cell is a tumor cell in vitro. In some instances, the cell is a tumor cell in vivo. In some instances, step (b) comprises performing: (i) cell proliferation or survival assay in vitro; and (ii) tumor formation, growth or metastasis assay in vivo.

In some instances, the expression or activity of the component is measured by microscopy imaging, Western blot, immunohistochemistry, ELISA, SPARCL, fluorescent signal detector, chromatography, radioactive binding assay, a fluorescence binding assay, a kinetic exclusion assay, a crystallography assay, PCR, or gel electrophoresis.

In some instances, the agent inhibits expression of a component of the nuclear pore complex. In some instances, the agent promotes degradation of a component of the nuclear pore complex. In some instances, the agent inhibits function of a component of the nuclear pore complex. In some instances, the agent modulates the expression of a regulator of the nuclear pore complex assembly. In some instances, the agent inhibits expression of a regulator of the nuclear pore complex assembly. In some instances, the agent modulates the function of a regulator of the nuclear pore complex assembly. In some instances, the agent inhibits function of a regulator of the nuclear pore complex assembly. In some instances, the agent modulates the expression of a regulator of the nuclear pore complex disassembly. In some instances, the agent modulates the function of a regulator of the nuclear pore complex disassembly. In some instances, the agent inhibits interaction between the components of nuclear pore complex. In some instances, the agent inhibits the recruitment of nucleoporins to the nuclear pore complex. In some instances, the agent inhibits the assembly of structure intermediates or pre-pores of nuclear pore complex. In some instances, the agent inhibits cell proliferation in malignant cells. In some instances, the agent inhibits cell proliferation in abnormally proliferative cells. In some instances, the agent induces cell death in malignant cells. In some instances, the agent induces cell death in abnormally proliferative cells.

In some instances, the agent inhibits Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the agent inhibits Nup35, Nup37, Nup43, Nup45, Nup50, Nup54, Nup58, Nup62, Nup75/85, Nup93, Nup96, Nup107, Nup133, Nup155, Nup160, Nup358, Seh1, Sec13, NDC1, Pom121, Nup210, Rael, HCG1/CG1, Aladin, TPR, or Elys of the nuclear pore complex. In some instances, the agent inhibits Nup35 of the nuclear pore complex. In some instances, the agent inhibits Nup37 of the nuclear pore complex. In some instances, the agent inhibits Nup43 of the nuclear pore complex. In some instances, the agent inhibits Nup45 of the nuclear pore complex. In some instances, the agent inhibits Nup50 of the nuclear pore complex. In some instances, the agent inhibits Nup54 of the nuclear pore complex. In some instances, the agent inhibits Nup58 of the nuclear pore complex. In some instances, the agent inhibits Nup62 of the nuclear pore complex. In some instances, the agent inhibits Nup75/85 of the nuclear pore complex. In some instances, the agent inhibits Nup93 of the nuclear pore complex. In some instances, the agent inhibits Nup96 of the nuclear pore complex. In some instances, the agent inhibits Nup107 of the nuclear pore complex. In some instances, the agent inhibits Nup133 of the nuclear pore complex. In some instances, the agent inhibits Nup155 of the nuclear pore complex. In some instances, the agent inhibits Nup160 of the nuclear pore complex. In some instances, the agent inhibits Nup358 of the nuclear pore complex. In some instances, the agent inhibits Seh1 of the nuclear pore complex. In some instances, the agent inhibits Sec13 of the nuclear pore complex. In some instances, the agent inhibits NDC1 of the nuclear pore complex. In some instances, the agent inhibits Pom121 of the nuclear pore complex. In some instances, the agent Nup210 of the nuclear pore complex. In some instances, the agent inhibits Rael of the nuclear pore complex. In some instances, the agent inhibits HCG1/CG1 of the nuclear pore complex. In some instances, the agent inhibits Aladin of the nuclear pore complex. In some instances, the agent inhibits TPR of the nuclear pore complex. In some instances, the agent inhibits Elys of the nuclear pore complex. In some instances, the agent inhibits a component of the nuclear pore complex comprising a protein binding pair, thereby disrupting the pair. In some instances, the protein binding/interacting pair is selected from a pair listed in Table 1. In some instances, the protein binding/interacting pair is selected from a pair listed in Table 2. In some instances, the protein binding/interacting pair is selected from a pair listed in Table 3. In some instances, the therapeutic agent targets the RNA or DNA of Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS of the nuclear pore complex. In some instances, the therapeutic agent binds to Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358 (RanBP2), Seh1, Sec13, NDC1, Pom121, Nup210, RAE1, HCG1/CG1(Nup12), Aladin, TPR, GLE1, and ELYS of the nuclear pore complex.

In some instances, the therapeutic agent is a small molecule. In some instances, the therapeutic agent is a small interfering RNA (siRNA). In some instances, the therapeutic agent is a short hairpin RNA (shRNA). In some instances, the therapeutic agent is a microRNA (miRNA). In some instances, the therapeutic agent is a messenger RNA (mRNA). In some instances, the therapeutic agent is a guideRNA (gRNA). In some instances, the therapeutic agent is an antisense oligonucleotide. In some instances, the therapeutic agent is a peptide. In some instances, the therapeutic agent is a peptidomimetic. In some instances, the therapeutic agent is an aptamer.

In some instances, the disease or disorder has abnormal nuclear transport. In some instances, the disease or disorder has normal nuclear transport. In some instances, the disease or disorder is a neoplastic disease. In some instances, the disease or disorder is caused by a malignant cell. In some instances, the disease or disorder is an inflammatory disease. In some instances, the disease or disorder is cancer. In some instances, the cancer has a mutation in the Ras gene. In some instances, the mutation is a G12D mutation. In some instances, cancer with G12D mutation is more sensitive to the agent. In some instances, the proliferative disease is atherosclerosis. In some instances, the proliferative disease is various forms of arthritis. In some instances, the proliferative disease is rheumatoid arthritis. In some instances, the proliferative disease is psoriasis. In some instances, the proliferative disease is various forms of fibrosis. In some instances, the proliferative disease is idiopathic pulmonary fibrosis. In some instances, the proliferative disease is scleroderma. In some instances, the proliferative disease is cirrhosis of the liver. In some instances, the proliferative disease is benign prostatic hyperplasia. In some instances, the proliferative disease is abnormal scar formation. In some instances, the proliferative disease is inflammatory bowel disease.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include a therapeutic agent disclosed herein, optionally with one or more additional therapeutic agents disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

These examples are provided for illustrative purposes only and not to limit the scope of the claims provided herein.

Example 1. Nuclear Pore Complex Assembly or Disassembly Assay in Animals

Animals, including but not limited to, mice, rats, fish are treated with nuclear pore complex (NPC) assembly and disassembly regulators including but not limited to small molecules, siRNAs, shRNAs, microRNAs, mRNAs, gRNA/CRISPR. The number of NPCs is analyzed in isolated tissues, cells and nuclei by directly measuring the amount of NPCs on nuclear membranes or the levels of NPC proteins or RNA in tissue or cell extracts.

The measurement of NPCs on nuclear membranes is performed in fixed or unfixed isolated cells, tissues, or nuclei. Fixed refers to treatment of cells, tissues or isolated nuclei with a fixative agent (such as formaldehyde, paraformaldehyde, glutaraldehyde, methanol, acetone, or other) before analysis. Visualization and quantification of NPC number/levels in the nuclear membranes of cells, tissues or nuclei is performed by direct or indirect antibody detection-coupled to a method to measure antibody levels such as microscopy imaging, ELISA, SPARCL, fluorescent signal detector. In the assay, primary antibodies that recognize one or more NPC components (including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS) are employed. Primary antibodies are directly labeled (direct assay) or used in combination with secondary detection systems such as secondary antibodies, biotin/streptavidin system, lumio.

For the analysis of nuclear pore assembly in cell, tissue or nuclei extracts, whole protein extracts or nuclear membrane protein extracts are prepared from tissues or cells of control and candidate-treated animals and the assembly of NPCs is determined by measuring protein levels for specific nuclear pore components. Protein levels are determined by western blot assays, ELISA, SPARCL, chromatography, mass spectrometry, or other means of quantifying specific protein levels.

To indirectly assay NPC assembly by measuring RNA levels, total RNA or mRNA is prepared from tissues or cells of treated animals and the expression levels of NPC components is determined by PCR, sequencing, hybridization methods, or other assays that allow to quantify specific RNA molecules.

Example 2. Nuclear Pore Complex Assembly or Disassembly Assay in Cultured Cells

The assembly or disassembly of nuclear pore complexes (NPCs) is followed by visualization of NPCs in the nuclear membranes of live or fixed cells or by measuring protein or RNA levels in cell extracts.

Live Cell Assays:

For live cells, the fluorescent signal of an endogenous NPC component tagged with a fluorescent marker (e.g GFP, RFP, Tomato or any other fluorescent tag), or of an ectopically expressed fluorescently-tagged NPC component, is used to visualize and quantify the number of NPCs at the nuclear membrane by the use of microscopy imaging. The increase or decrease in the signal of NPCs in cells is employed to discover molecules that activate or inhibit NPC assembly.

Dividing cells expressing an endogenously tagged NPC component (generated by inserting a fluorescent tag in frame with the endogenous gene of NPCs member e.g. by using CRISPR technology), or dividing cells ectopically expressing tagged NPC component (such as a cell line generated by insertion of a plasmid carrying the nuclear pore component fused in frame with a fluorescent tag) are grown in multi-well culture plates at low density. Cells are incubated with potential regulators of NPC assembly and disassembly (small chemical entities, siRNA, shRNAs, microRNAs, mRNA, gRNA/CRISPR, or others) for 2-5 days and quantified using microscopy imaging (epifluorescent microscope, confocal microscope, spinning disk microscope, light sheet microscope, or similar) or other methods of measuring fluorescent signals. The signal for NPCs in cells is quantified using computer software.

Fixed Cell Assays:

For fixed cells, the amount of NPCs is determined by direct or indirect immunofluorescence using antibodies that recognize one or more NPC components (including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS) or antibodies that recognize the tag fused to the NPC component (fluorescent tag such as GFP, RFP, CFP, TOMATO, antibody tag e.g HA, MYC, FLAG, or others e.g. biotin, lumino, etc). Primary antibodies are labeled with a fluorescent molecule (e.g. FITC, CYS, Alexa fluor, quantum dots) or used in combination with labeled secondary antibodies or other chemical entities used for detection (such as streptavidin). Quantification of NPC number in cells is performed by microscopy imaging, ELISA, SPARCL, fluorescent signal detector, or other means of detecting antibodies, light or chemical signals.

Dividing cells expressing an endogenously tagged NPC component (generated by inserting a fluorescent tag in frame with the endogenous gene of NPCs member e.g by CRISPR technology), or dividing cells ectopically expressing a tagged NPC component (such as a cell line generated by insertion of a plasmid carrying the nuclear pore component fused in frame with a fluorescent tag) are grown in multi-well culture plates at low density. Cells are incubated with potential regulators of NPC assembly and disassembly (small chemical entities, siRNA, shRNAs, microRNAs, mRNA, gRNA/CRISPR, or others) for 2-5 days and fixed. The number of NPCs is quantified using microscopy imaging (epifluorescent microscope, confocal microscope, spinning disk microscope, light sheet microscope, or similar) or other methods of measuring fluorescent signals. The signal for NPCs in cells is quantified using computer software. Alternatively, antibodies that recognize the tag fused to the NPC component (fluorescent tag such as GFP, RFP, CFP, TOMATO, antibody tag e.g HA, MYC, FLAG, or others e.g. biotin, lumino, etc). are used after fixation to enhance the NPC fluorescent signal. Primary antibodies are labeled with a fluorescent molecule (e.g. FITC, CYS, Alexa fluor, quantum dots) or used in combination with labeled secondary antibodies or other chemical entities used for detection (such as streptavidin). Quantification of NPC number in cells is performed by microscopy imaging, ELISA, SPARCL, fluorescent signal detector, or other means of detecting antibodies, light or chemical signals.

Alternatively, unmodified dividing cells are grown for 2-5 days in the presence of potential regulators of NPC assembly (small chemical entities, siRNA, shRNAs, microRNAs, mRNAs, gRNA/CRISPR, or others). Cells are fixed and nuclear complexes are analyzed either by direct immunofluorescence using primary antibodies that recognize a NPC component (including, but not limited to, Nup35, Nup37, Nup43, Nup45, Nup50, Nup54, Nup58(Nup11), Nup62, Nup75/85, Nup88, Nup93, Nup96, Nup98, Nup107, Nup133, Nup153, Nup155, Nup160, Nup188, Nup205, Nup214, Nup358(RanBP2), Seh1, Sec13, NDC1, Pom121, Nup210, RAE1, HCG1/CG1(Nup12), Aladin, TPR, GLE1, and ELYS) labeled with a fluorescent dye; or indirect immunofluorescence using a secondary antibody or other chemical entities used for detection (such as streptavidin). Alternatively, cell proliferation and cell death is also measured as a result of inhibition of nuclear pore assembly.

Cell Extracts:

For the analysis of nuclear pore assembly in cell extracts, whole cell or nuclear membrane protein extracts are prepared from cells treated with control and candidate molecules and the assembly of NPCs is followed by western blot assays, ELISA, SPARCL, chromatography, mass spectrometry, or any other mean of quantifying specific protein levels.

Dividing cells are grown for 2-5 days in the presence of potential regulators of NPC assembly (small chemical entities, siRNA, shRNAs, microRNAs, mRNAs, gRNA/CRISPR, or others). Cells are collected and whole cell or nuclear membrane protein extracts are prepared using conventional protein extraction methods. The assembly of NPCs is followed by western blot assays, ELISA, SPARCL, chromatography, mass spectrometry, or any other mean of quantifying specific protein levels.

To assay NPC assembly by measuring RNA levels, total RNA or mRNA is prepared from treated cells and the expression levels of NPC components is determined by PCR, RNA sequencing, hybridization methods, or other assays that allow to quantify specific RNA molecules.

Example 3. Indirect Nuclear Pore Complex Assembly Assay In Vitro

Nuclear pore complex (NPC) assembly relies on the interaction of different components of the structure and their recruitment to the nuclear membranes. Preventing the interaction between nucleoporins also inhibits NPC assembly. To identify molecules that prevent the interaction or association of NPC components, native or tagged nucleoporin proteins are produced in bacteria, yeast, mammalian cells, cell-free transcription/translation systems, or other systems that allow recombinant protein production and purified using conventional purification methods (such as liquid chromatography, affinity purification columns, etc). Purified nucleoporins are combined with potential regulators of protein-protein interaction (e.g. small molecules) and the association dissociation of protein complexes is determined using standard protein-protein interaction detection methods, such as methods based on crystal resonance or quartz crystal microbalance (QCM), surface plasmon resonance (SPR, e.g. Biacore), scanning tunneling microscopy (STM), total internal reflection fluorescence (TIRF), isothermal titration calorimetry (ITC), differential scanning calorimetry (DSC), fluorescence resonance energy transfer, atomic force microscopy (AFM), or any other method that allows measuring protein-protein interactions. Alternatively, interaction between nucleoporins is measured in cell extracts instead of isolated proteins.

Example 4. Indirect Nuclear Pore Complex Assembly Assay In Vivo

Nuclear pore complex (NPC) assembly relies on the interaction of different components of the structure and their recruitment to the nuclear membranes. Preventing the interaction between nucleoporins also inhibits NPC assembly. To identify molecules that prevent the interaction or association of NPC components in vivo, interacting nucleoporin proteins or nucleoporin protein fragments fused to tags that allow to detect their association are produced in bacteria, yeast, mammalian cells, multicellular organisms (such as *C. elegans*, Zebrafish, *Drosophila*) or other systems that allow ectopic protein expression. Cells are combined with potential regulators of protein-protein interaction (e.g. small molecules) and the association/dissociation of protein complexes is determined using standard protein-protein interaction detection methods, such as methods based on Fluorescence resonance energy transfer (FRET), Bioluminescence Resonance Energy Transfer (BRET), Bimolecular Fluorescence Complementation (BiFC), Protein-fragment complementation assay (PCA) or any other method that allows measuring protein-protein interactions in cells. Protein tags that are combined with nucleoporin proteins or nucleoporin protein fragments include, but are not limited to, fluorescent tags that allow energy transfer for FRET or BRET (EBFP2, EGFP, ECFP, EYFP, Cerulean, Venus, MiCy, mKO, TFP1, mVenus, CyPet, YPet, mCherry, Venus, tdTomato, mPlum, TagBFP, TagGFP2, TagGFP2, TagRFP, TurboFP, mOrange Luciferase, NanoLuc), or split proteins for BIFC or PCA (split-Beta-lactamase, split-Dihydrofolate reductase (DHFR), split-Focal adhesion kinase (FAK), split-Gal4 transcription factor, split-GFP, split-YFP, split-CFP, split-Horseradish peroxidase (HRP), split-Infrared fluorescent protein IFP1.4, split-LacZ beta-galactosidase, split-Luciferase, recombinase enhanced bimolecular luciferase (ReBiL), NanoLuc, and NanoBIT, split-TEV (Tobacco etch virus protease) and split-Ubiquitin). Alternatively, interaction between nucleoporins is measured in cell extracts instead of live cells proteins.

Example 5. Nuclear Pore Complex Component Depletion in Cultured Cells

Figure 2A:
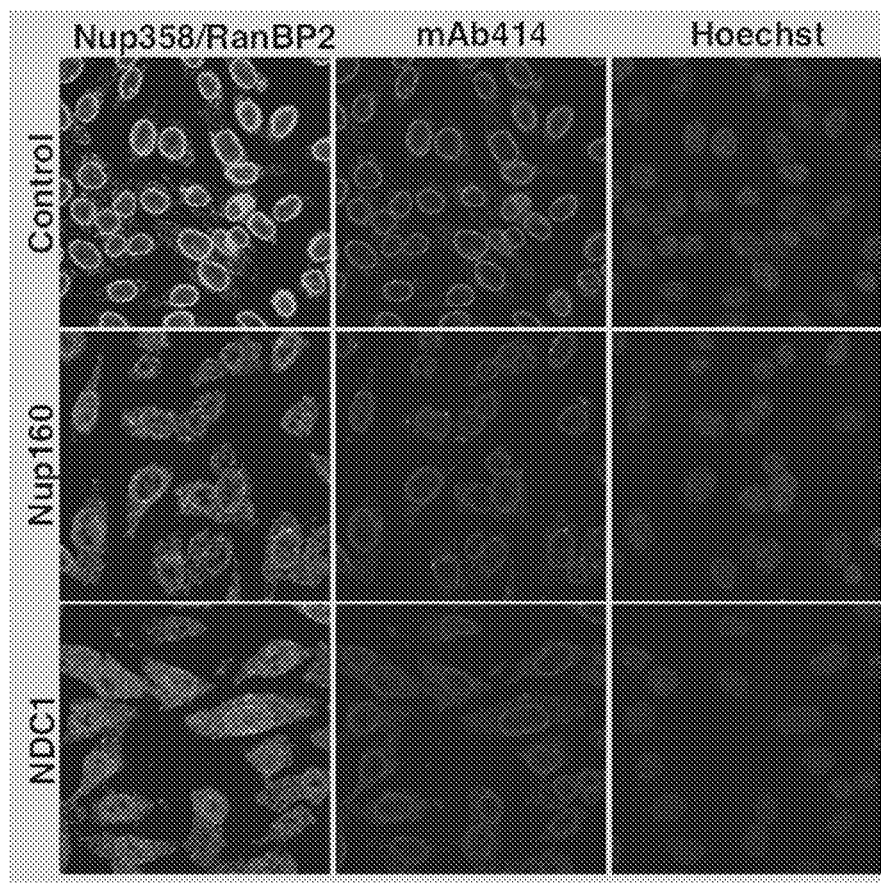
FIG. 2A exemplifies the depletion of essential NPC components (Nup160 and NDC1) using specific shRNAs inhibits NPC assembly.
Figure 2B:
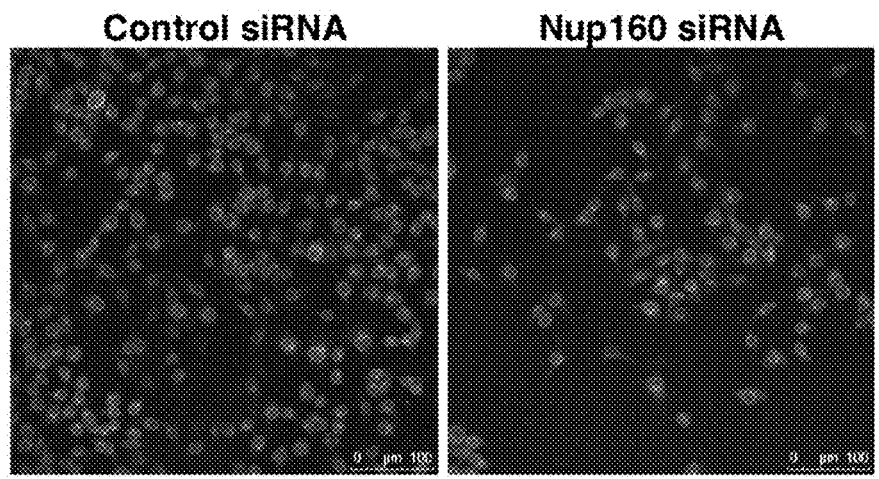
FIG. 2B exemplifies inhibition of NPC assembly with siRNA against Nup160 inhibits cell proliferation and reduces cell number.

A375 cells were infected with lentivirus carrying Control, Nup160 or NDC1 shRNAs and selected to obtain stable cell lines (FIG. 2A), or transfected with Control or Nup160 specific siRNAs (FIG. 2B). Cells were allowed to proliferate for 3 days, fixed and stained with antibodies against different nuclear pore components. mAb414 recognizes Nup358, Nup214, Nup153 and Nup62. Anti-Nup358 recognizes Nup358.

Example 6. Inhibition of Nuclear Pore Complex Assembly with shRNAs

Figure 3A:
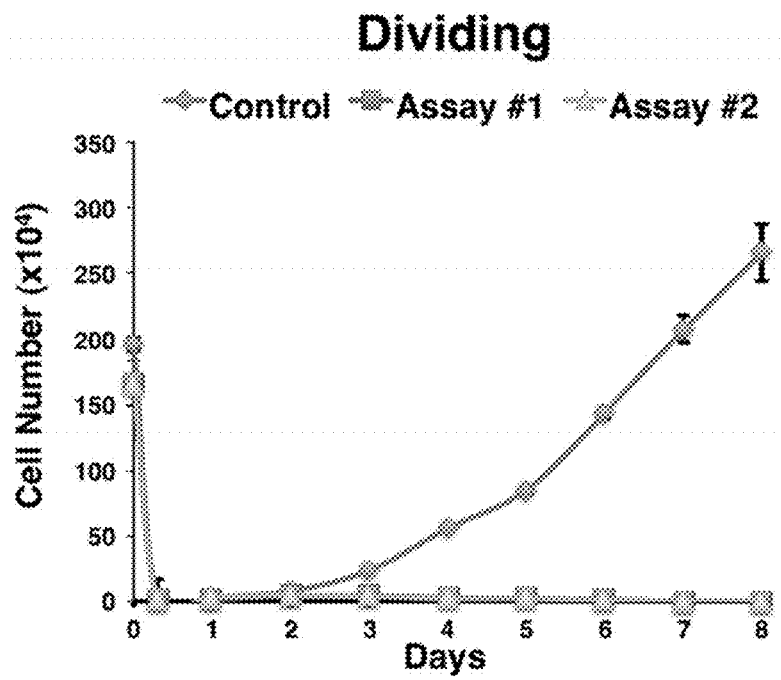
FIG. 3A-3B exemplifies that inhibition of NPC assembly with shRNAs against core nuclear pore complex components important for NPC assembly (assay 1: Nup160 and assay 2: NDC1) blocks the proliferation of cancer cells (FIG. 3A), but does affect non-dividing/slow dividing cells (FIG. 3B).
Figure 3B:
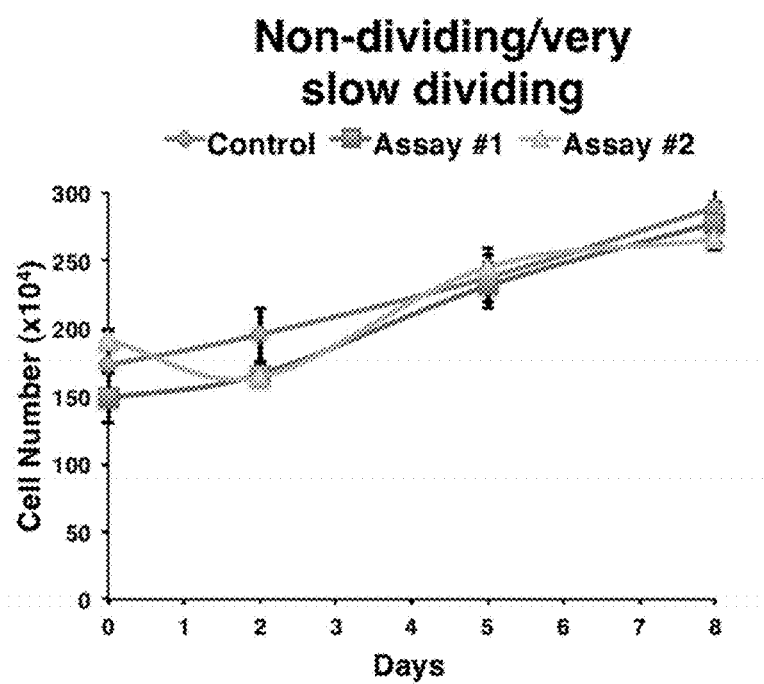
Figure 4A:
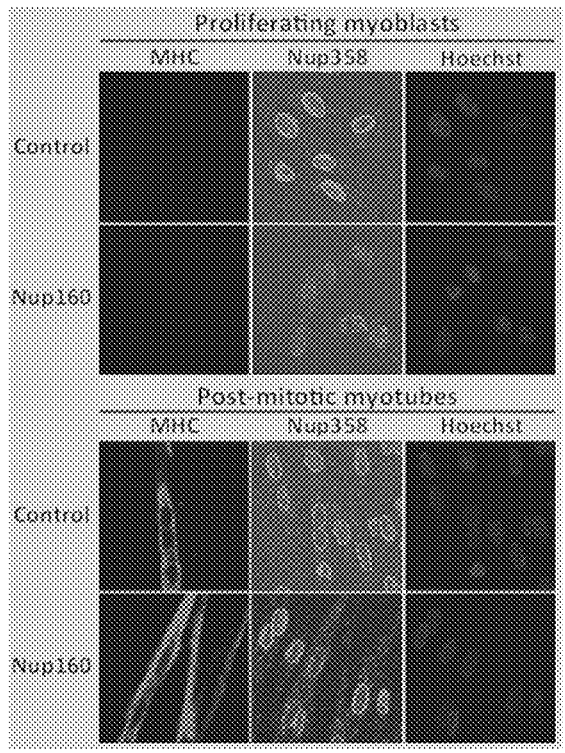
FIG. 4A exemplifies that inhibition of nuclear pore assembly depletes nuclear pores from proliferating myoblasts but not differentiated muscle cells.
Figure 4B:
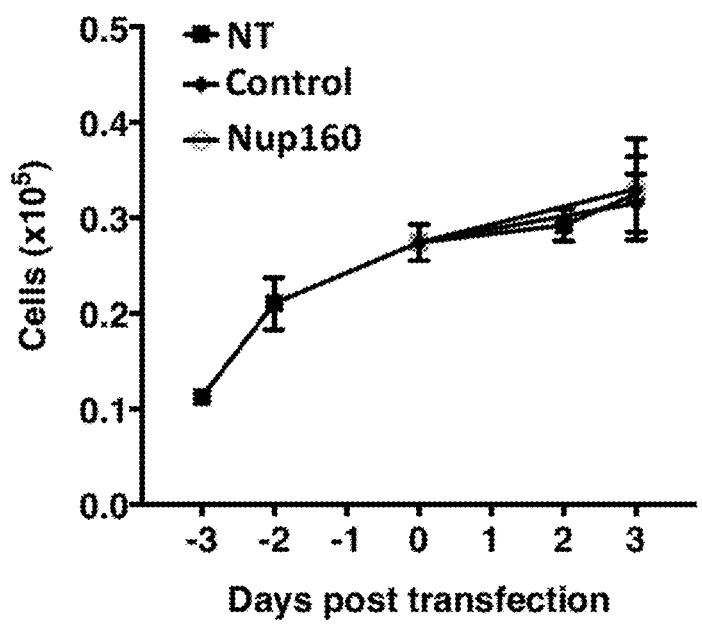
FIG. 4B exemplifies that inhibition of nuclear pore assembly has no or little effect on slow proliferating cells.
Figure 5A:
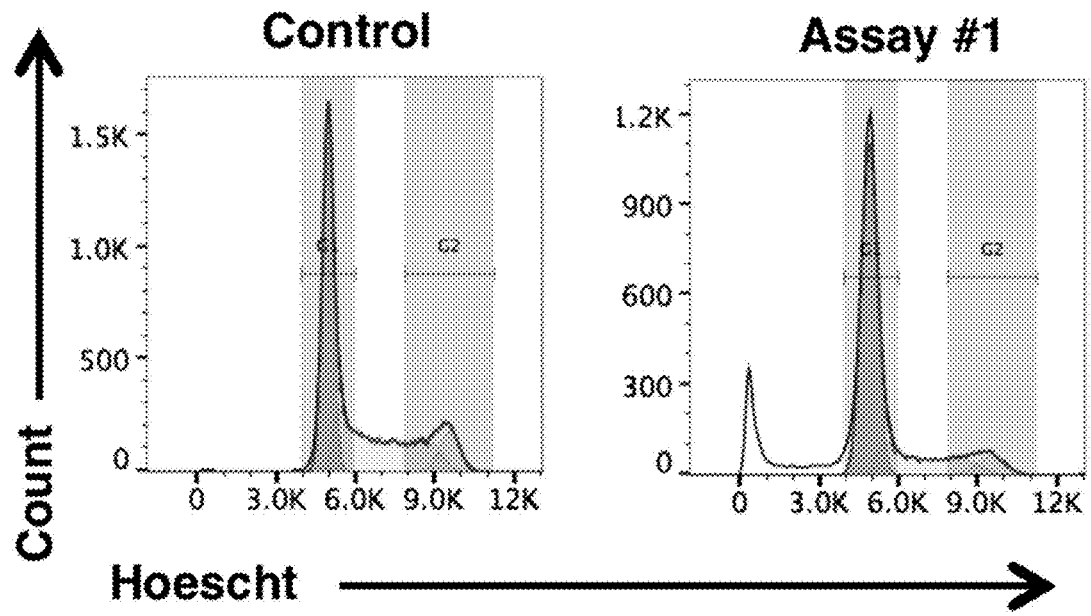
FIG. 5A exemplifies cell cycle analysis of A375 cells treated with Control or Nup160 shRNAs to inhibit nuclear pore complex assembly. Inhibition of NPC assembly increases the population of cells is subG1 (dead/dying cells).
Figure 5B:
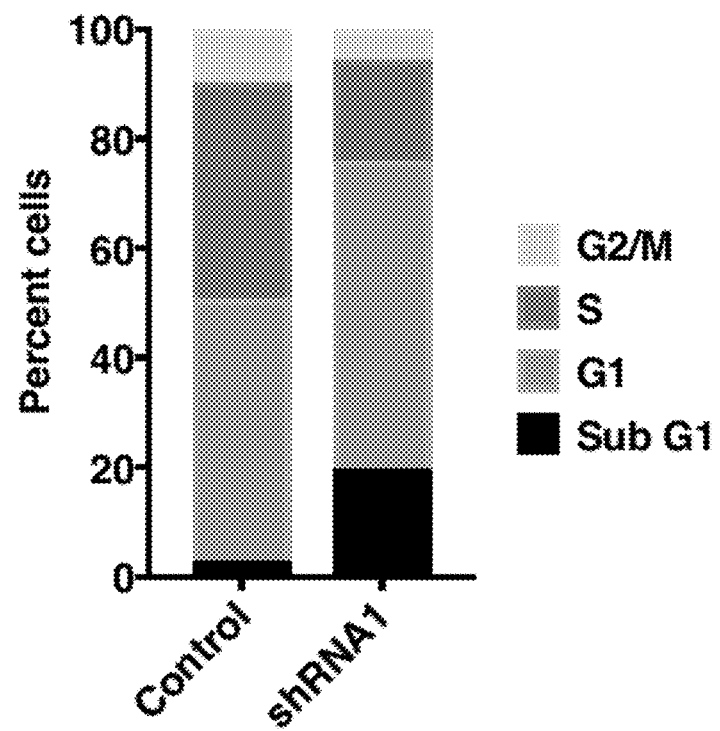
FIG. 5B is an exemplary quantification of cells in different phases from FIG. 5A.
Figure 6A:
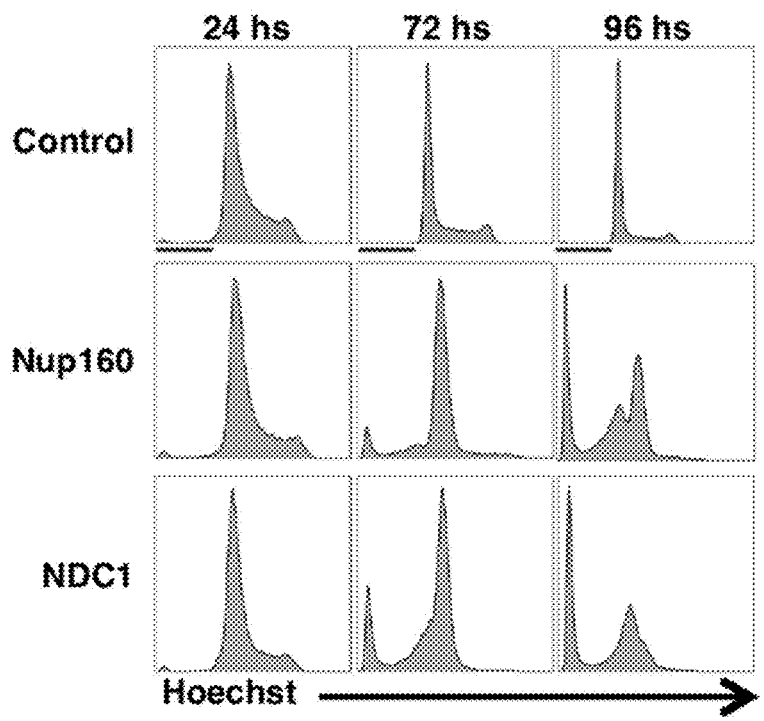
FIG. 6A exemplifies cell cycle analysis of Control, Nup160-depleted or NDC1-depleted A375 cells at different times after release from cell cycle synchronization. Inhibition of NPC assembly increases the population of cells is subG1 (black bar) over time. SubG1 cells correspond to dying/dead cells.
Figure 6B:
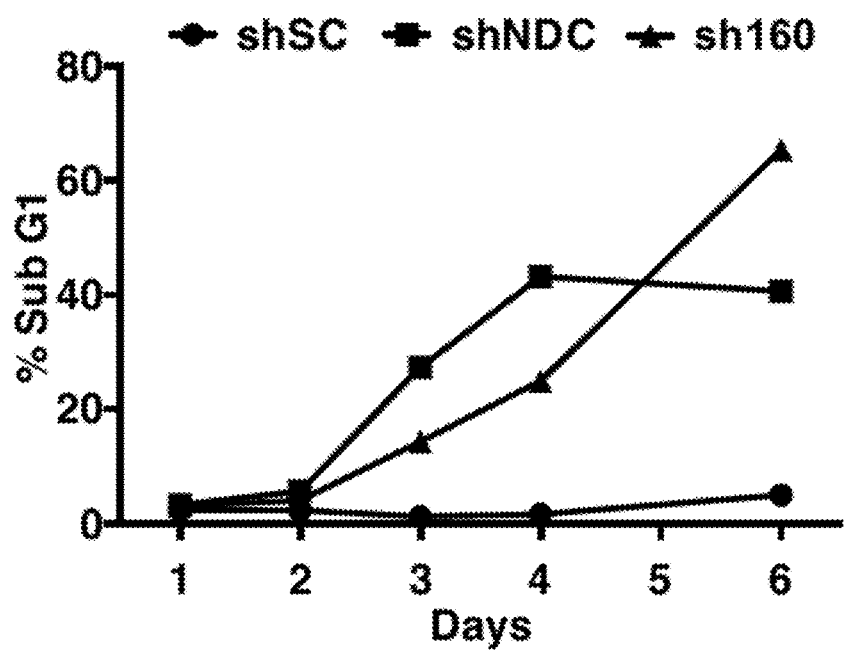
FIG. 6B is an exemplary quantification of the % of SubG1 cells in Control, Nup160-depleted or NDC1-depleted at different times after depletion.

A375 cells were infected with lentivirus carrying inducible Control, Nup160 or NDC1 shRNAs and selected to obtain stable cell lines. Cells were allowed to grow to confluency and shRNA was induced with doxycycline for 48 hours. Cells were either replated at 1:10 dilution to allow proliferation (FIG. 3A), or kept at confluency (FIG. 3B), and cell number was measured for 8 days.

Example 7. Inhibition of Nuclear Pore Complex Assembly with shRNAs

Proliferating or post-mitotic cells were treated with control or Nup160 shRNAs to inhibit nuclear pore assembly and stained with antibodies against myotubes (MHC) and nuclear pore complexes (Nup358). Hoechst was used as nuclear marker. Cell proliferation was slowed down by growing cells in low-serum media and cell number was measured over time. Control or Nup160 shRNAs were induced at time 0.

Example 8. Cell Cycle Analysis of Cells with Inhibited Nuclear Pore Complex Assembly A375 cells expressing inducible Control or Nup160 shRNAs were synchronized for 16 hours in the presence of doxycycline to induce shRNA expression. Cells were released, allowed to grow for 72 hours and stained with Hoechst. Cell cycle progression was analyzed by flow cytometry.

Example 9. Cell Cycle Analysis of Cells with Inhibited Nuclear Pore Complex Assembly A375 cells expressing tetracycline-inducible Control, Nup160 or NDC1 shRNAs were synchronized for 16 hours in the presence of doxycycline to induce shRNA expression. Cells were released, allowed to grow for 24, 72 or 96 hours and stained with Hoechst. Cell cycle progression was analyzed by flow cytometry.

Example 10. Apoptosis in Cells with Inhibited Nuclear Pore Complex Assembly

Figure 7A:
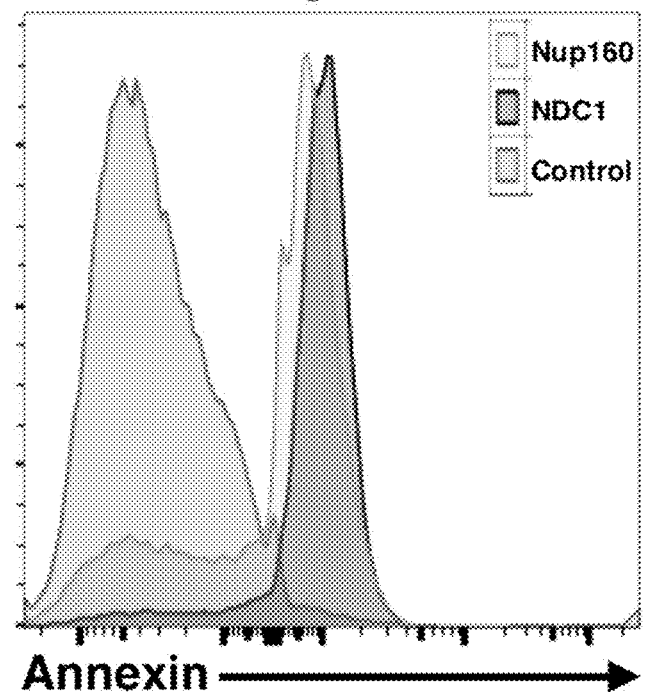
FIG. 7A-7B exemplify the increase in apoptotic cells in A375 cells depleted of the nuclear pore complex Nup160 or NDC1, which are required for pore assembly, when compared to the A375 Control cells when stained with the apoptotic marker Anexin V on day 6 after knockdown induction.
Figure 7B:
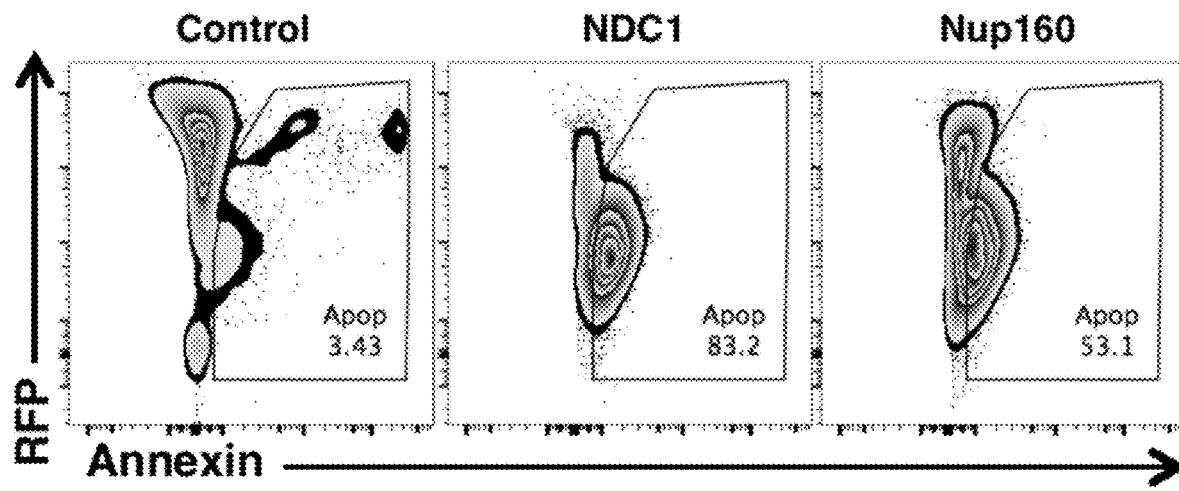
Figure 7C:
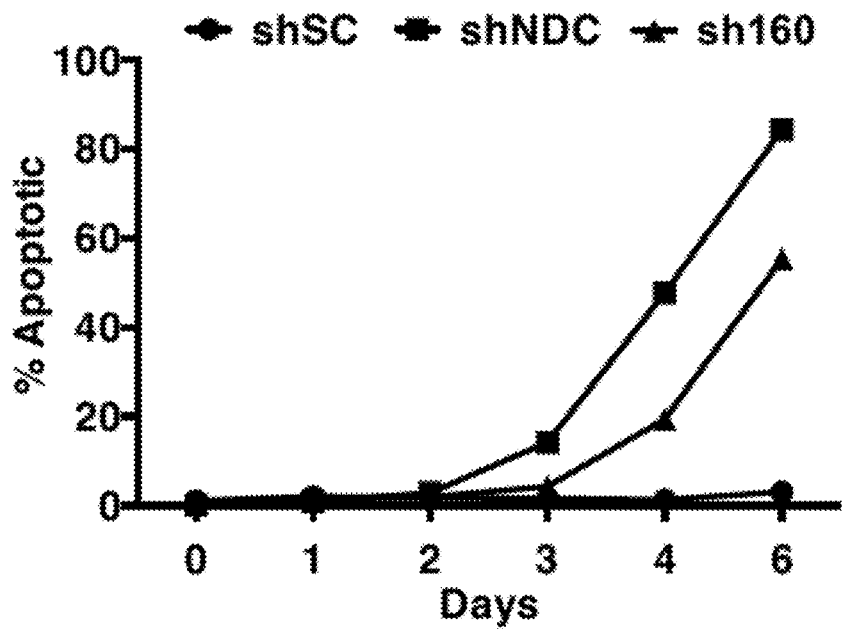
FIG. 7C is an exemplary percentage of apoptotic cells in proliferating cultures of Control, Nup160-depleted or NDC1-depleted cells quantified over time.
Figure 7D:
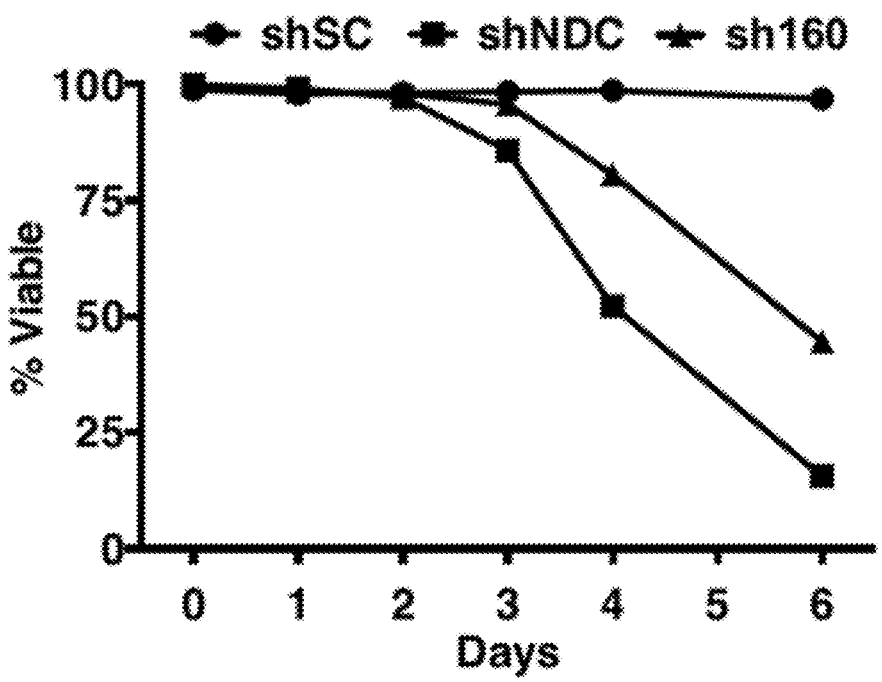
FIG. 7D illustrates cell viability of Control, Nup160-depleted or NDC1-depleted cells quantified over time.
Figure 8A:
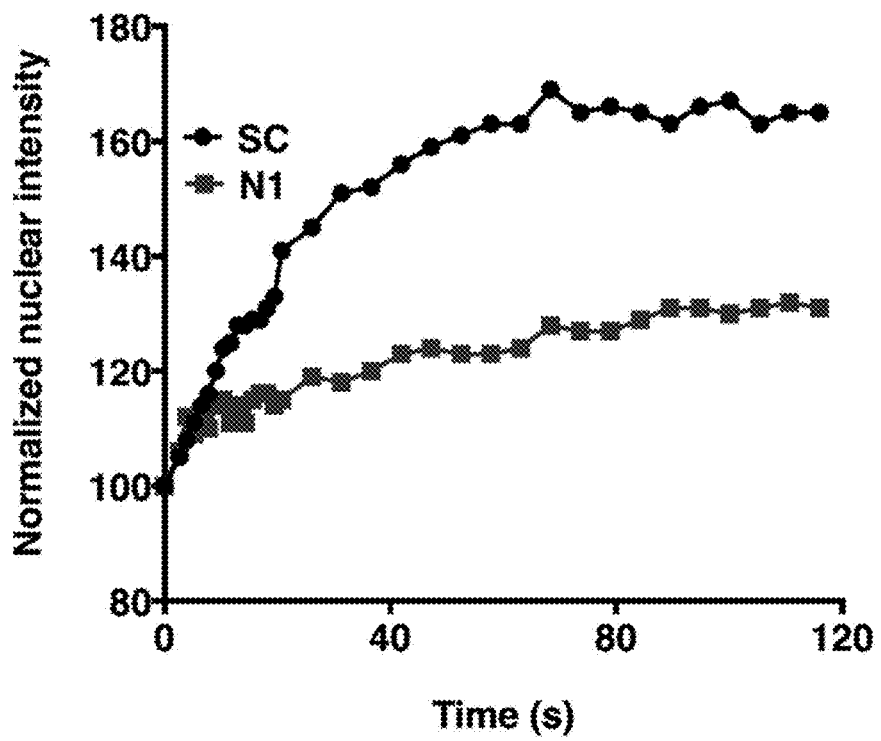
FIG. 8A-8B exemplifies the measurement of nuclear import rates in A375 skin melanoma cancer cells using the nuclear transport reporter NLS-tomato-NES by fluorescence recovery after photobleaching (FRAP). A375 cells expressing control (SC) or Nup160 (N1) shRNAs were transfected with the NLS-tomato-NES nuclear transport reporter and nuclear import was measured by Fluorescence recovery after photobleaching (FRAP).
Figure 8B:
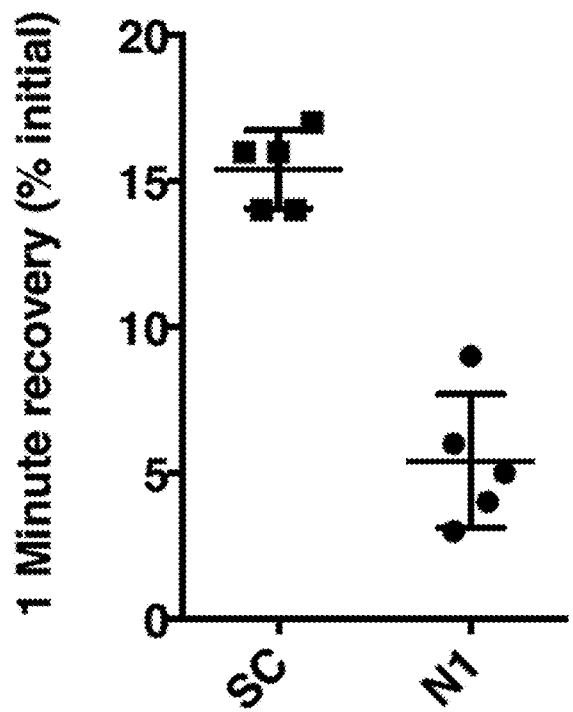
Figure 9:
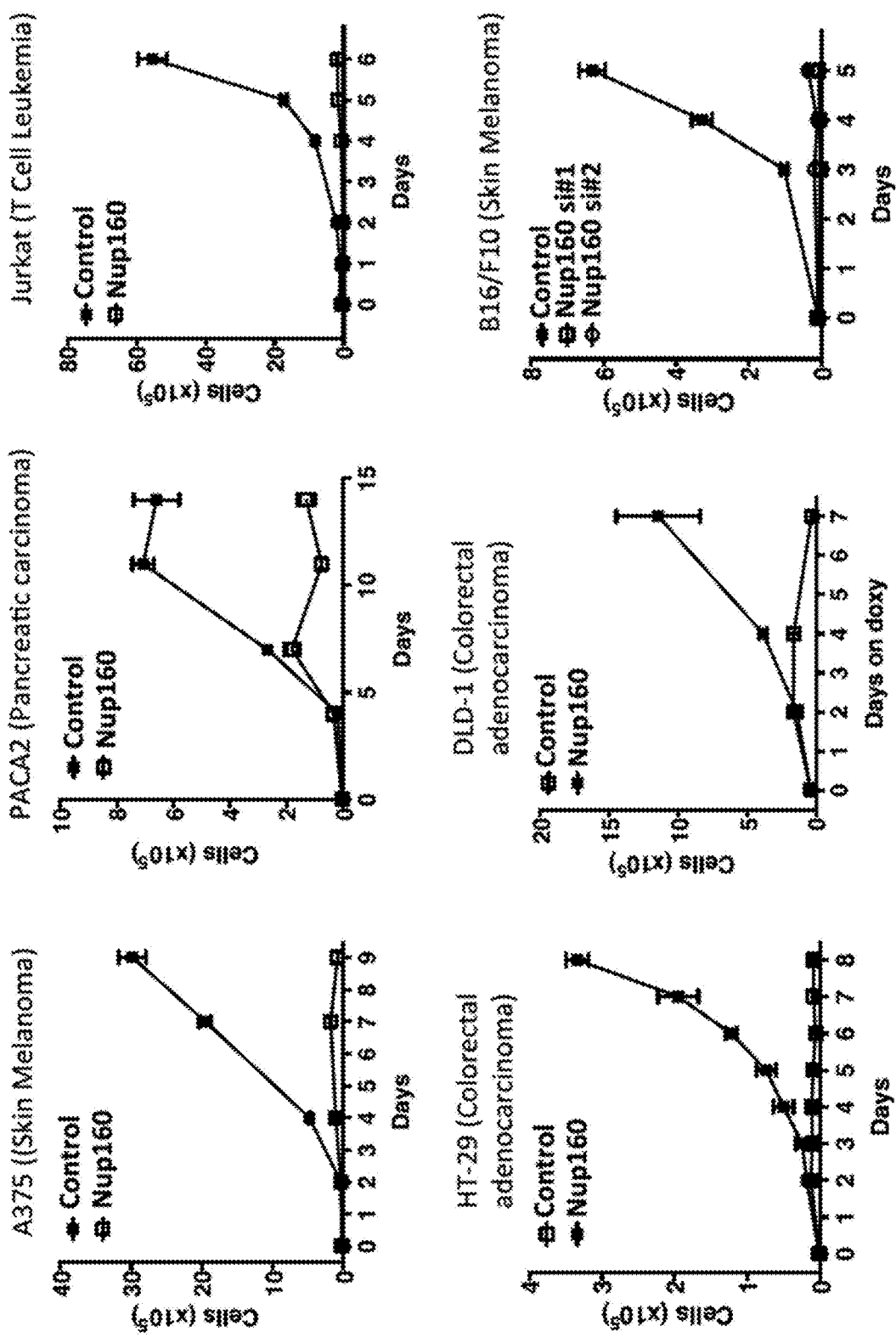
FIG. 9 exemplifies that inhibition of nuclear pore assembly inhibits cell proliferation and induces cell death in different cancer cells.

A375 cells expressing tetracycline-inducible Control, Nup160 or NDC1 shRNAs were synchronized for 16 hours in the presence of doxycycline to induce shRNA expression. Cells were released, allowed to grow. Anexin V (FIG. 7A-7B) and cell death marker (FIG. 7C) staining coupled to flow cytometry was used to determine the percentage of apoptotic and viable cells at different times after induction of knockdown.

Example 11. Cell Proliferation and Cell Death in Cancer Cells with Inhibited Nuclear Pore Assembly Different cancer cell lines were infected with control or Nup160 shRNAs to block nuclear pore assembly and cell number was measured over time. All cell lines are human with the exception of B16/F10 which is mouse. B16/F10 cells were transfected with control or Nup160 siRNAs and cell proliferation was determined by measuring cell number over time.

Example 12. Tumor Growth in Cancer Cells with Inhibited Nuclear Pore Assembly

HT-29 colorectal cancer cells carrying tetracycline inducible control or Nup160 shRNAs were injected subcutaneously in NOD-SCID immunodeficient mice. Tumors were allowed to grow to 50-100 mm$^3$ and shRNA was induced by feeding the animals with doxycycline on Day 14. Tumor volume was measured over time and/or at the end of treatment.

After treatment, tumors were isolated, sectioned and stained with an antibody against the nuclear pore complex component Nup98 and with Hoechst to stain the nucleus.

Example 13. Tumor Growth in Cancer Cells with Inhibited Nuclear Pore Assembly

A375 skin melanoma cancer cells carrying tetracycline inducible control or Nup160 shRNAs were injected subcutaneously in NOD-SCID immunodeficient mice.

Tumors were allowed to grow to 50-100 mm$^3$ and shRNA was induced by feeding the animals with doxycycline on Day 9. Tumor volume or weight was measured over time.

Example 14. Effect of Inhibition of Nuclear Pore Complex Assembly on Cancer and Normal Cells A375 melanoma cancer cells and IMR90 normal fibroblasts were infected with lentivirus carrying inducible Control or Nup160 shRNAs (N1) and selected to obtain stable cell lines. shRNA expression was induced with doxycycline and cell number was determine over the course of 7 days.

Example 15. Cancer Cells Carrying Ras Mutation are More Sensitive to Inhibition of Nuclear Pore Assembly DLD-1 colorectal cancer cells carrying wild type or mutated Ras (G12D) were infected with lentivirus carrying inducible Control or Nup160 shRNAs and selected to obtain stable cell lines. shRNA expression was induced with doxycycline and cell number was determine over the course of 7 days.

Example 16. Inhibition of Nuclear Pore Complex Assembly

Figure 10:
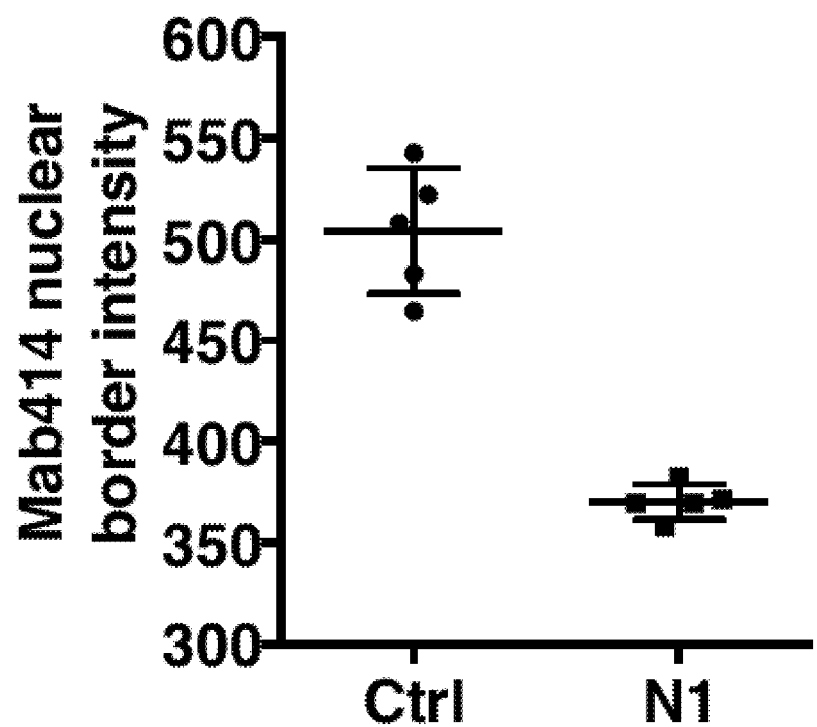
FIG. 10 is an exemplary quantification of the reduction in the signal for NPCs at the surface of the nucleus when nuclear pore assembly is inhibited by Nup160 depletion.
Figure 11:
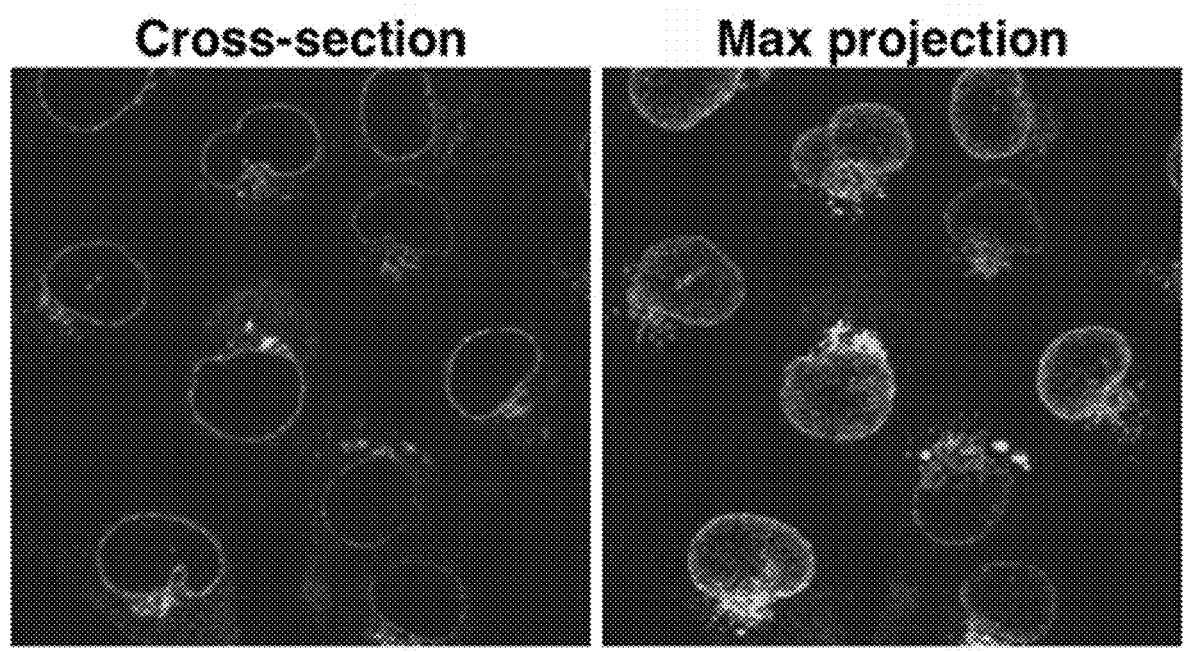
FIG. 11 illustrates cells expressing and endogenous nuclear pore complex component tagged with GFP using CRISPR technology imaged by confocal microscopy.
Figure 12:
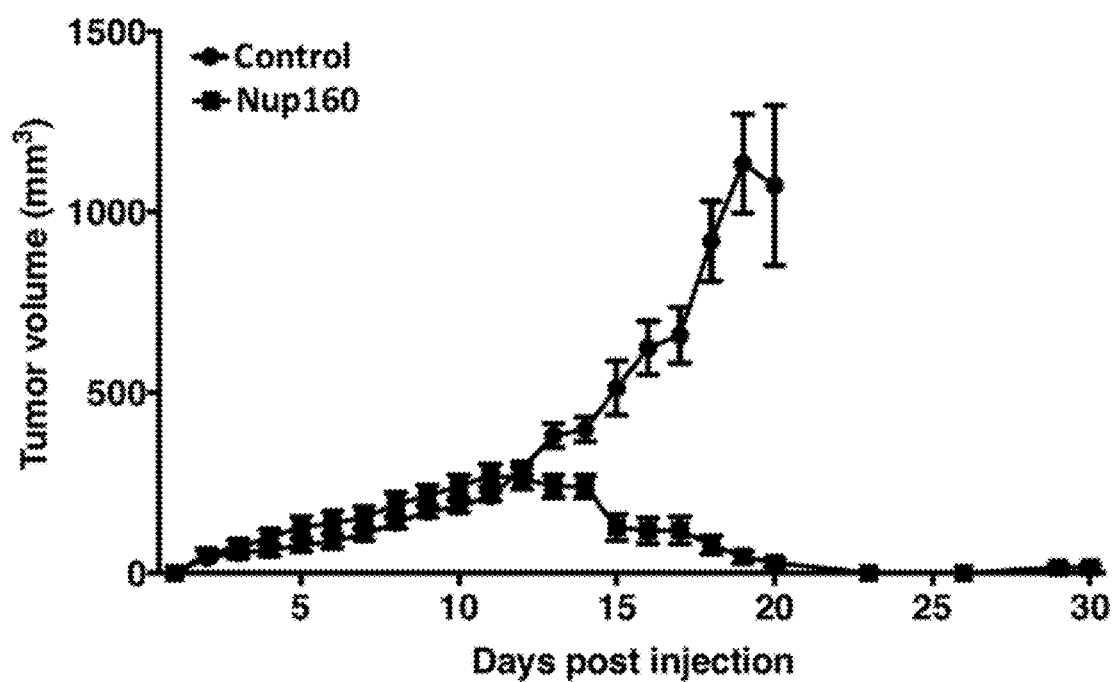
FIG. 12 illustrates tumor growth over time before or after the induction of Nup160 shRNA (Day 14). Inhibition of nuclear pore assembly by Nup160 depletion inhibits tumor growth and results in tumor remission.
Figure 13:
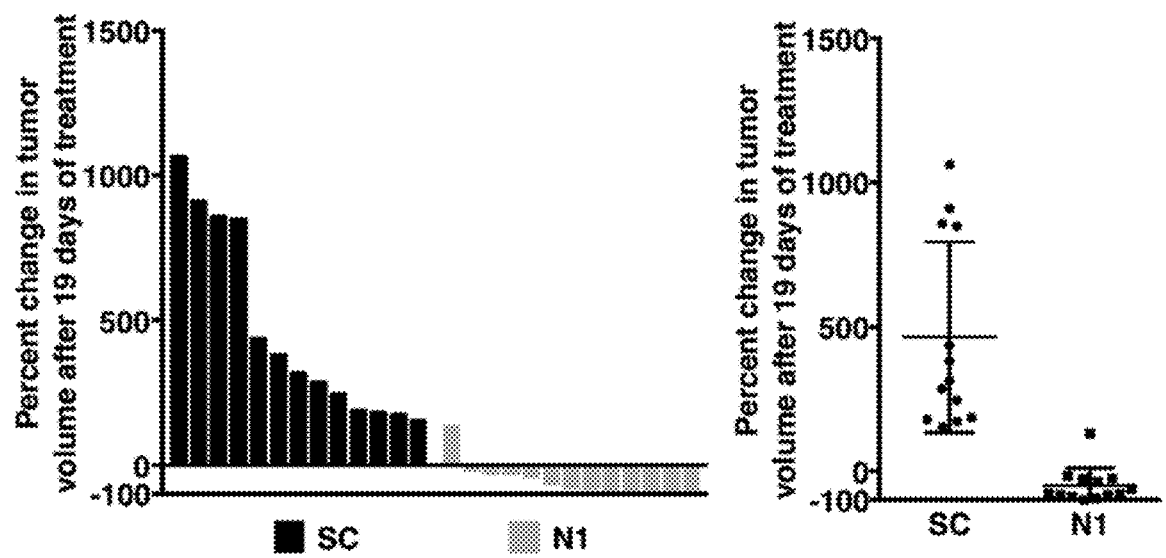
FIG. 13 illustrates percentage change in tumor volume from the start to the end of treatment (inhibition of nuclear pore assembly). Inhibition of nuclear pore assembly inhibits tumor growth and results in tumor remission.
Figure 14A:
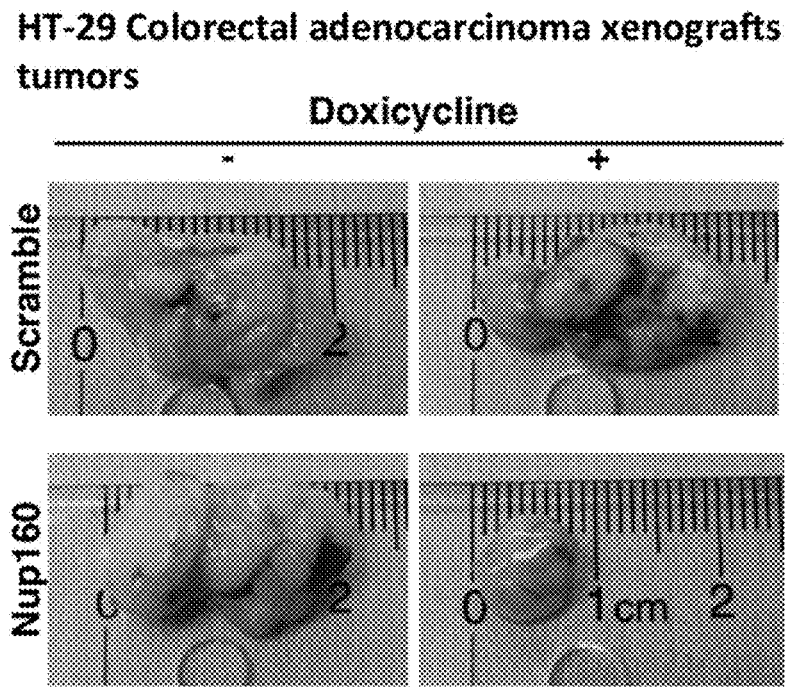
FIG. 14A-14B exemplify inhibition of nuclear pore assembly results in smaller tumors than controls when Control or Nup160-depleted tumors were isolated at the end of treatment and their volumes were measured.
Figure 14B:
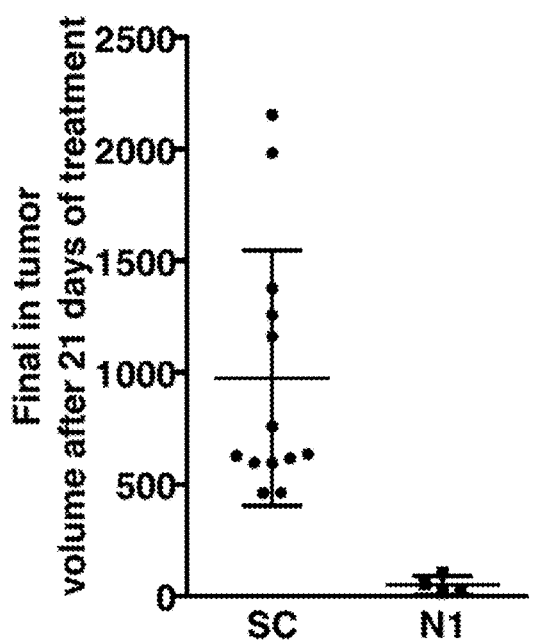
Figure 15:
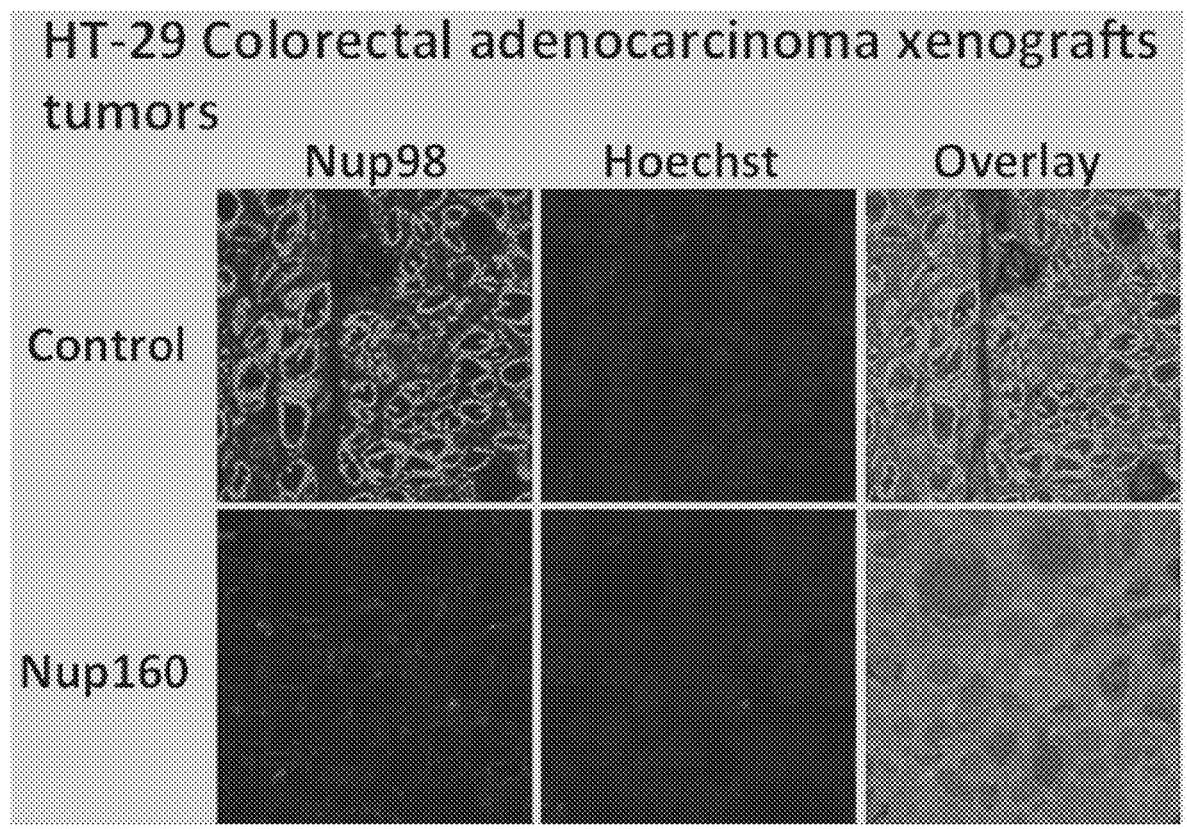
FIG. 15 exemplifies depletion of Nup160 in HT-29-induced tumors results in strong inhibition of nuclear pore complex assembly in vivo.
Figure 16:
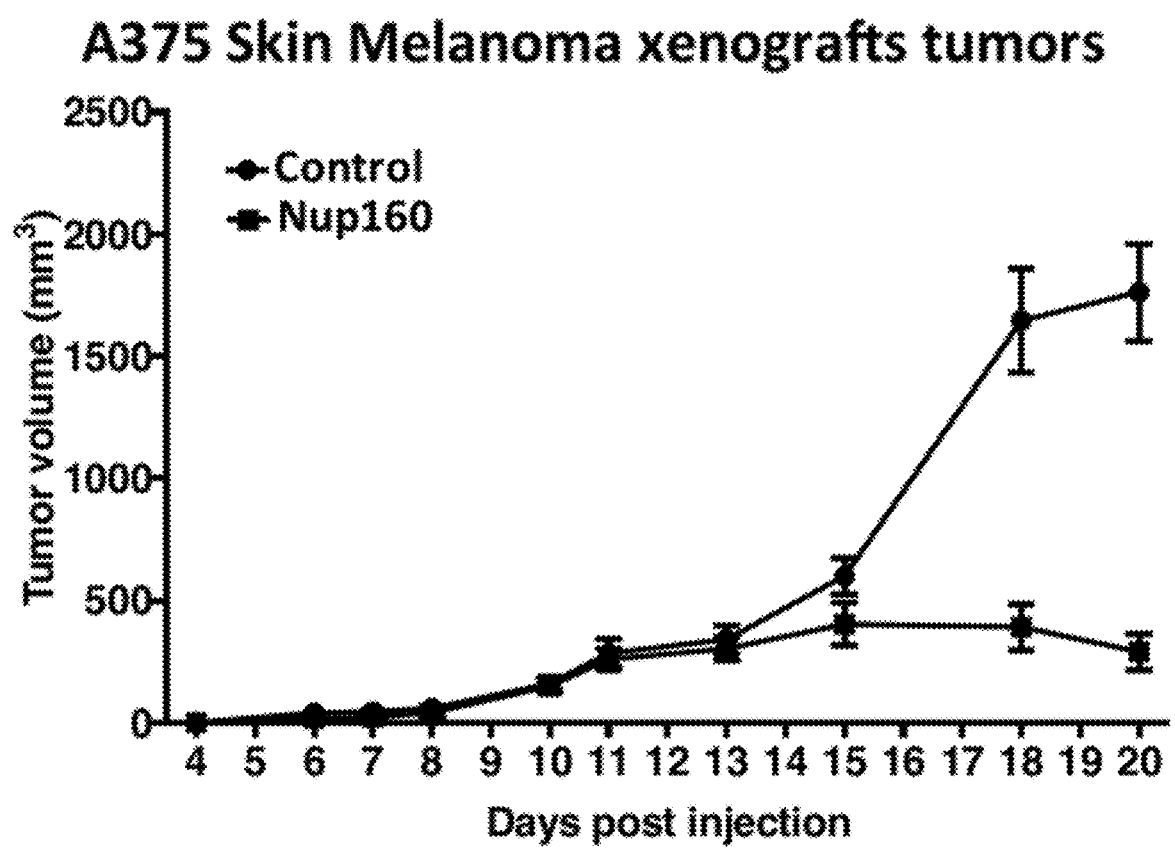
FIG. 16 illustrates tumor growth over time before or after the induction of Nup160. Inhibition of nuclear pore assembly by Nup160 depletion inhibits tumor growth and results in tumor remission.
Figure 17:
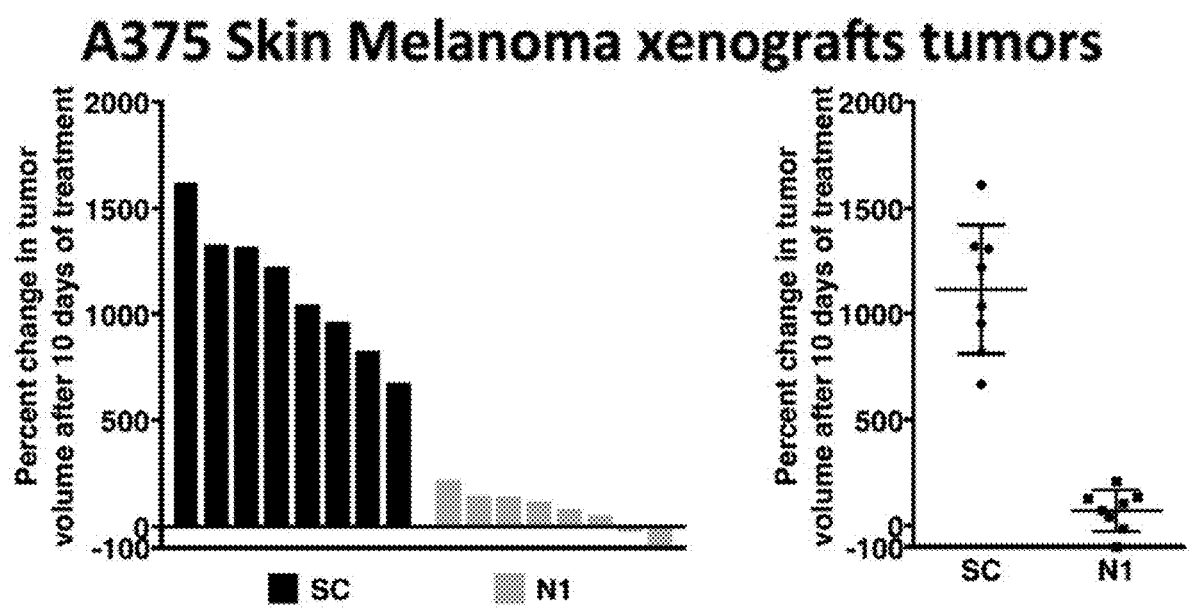
FIG. 17 illustrates percentage change in tumor volume from the start to the end of treatment (inhibition of nuclear pore complex assembly). Inhibition of nuclear pore assembly inhibits tumor growth and results in tumor remission.
Figure 18A:
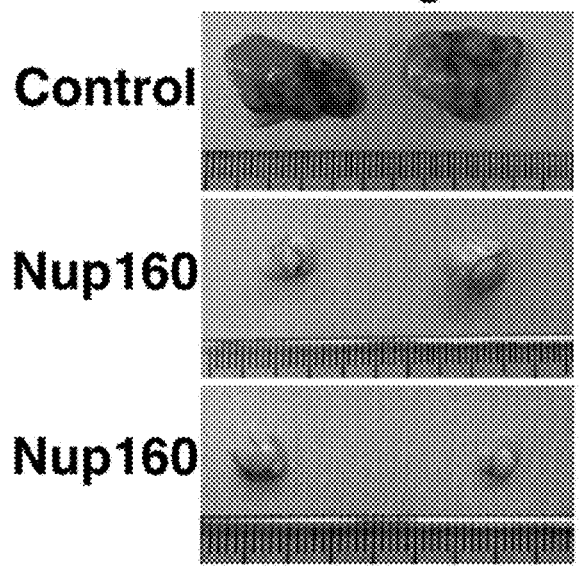
FIG. 18A-18B exemplify inhibition of nuclear pore assembly results in smaller tumors than controls when Control or Nup160-depleted tumors were isolated at the end of treatment and their weights measured.
Figure 18B:
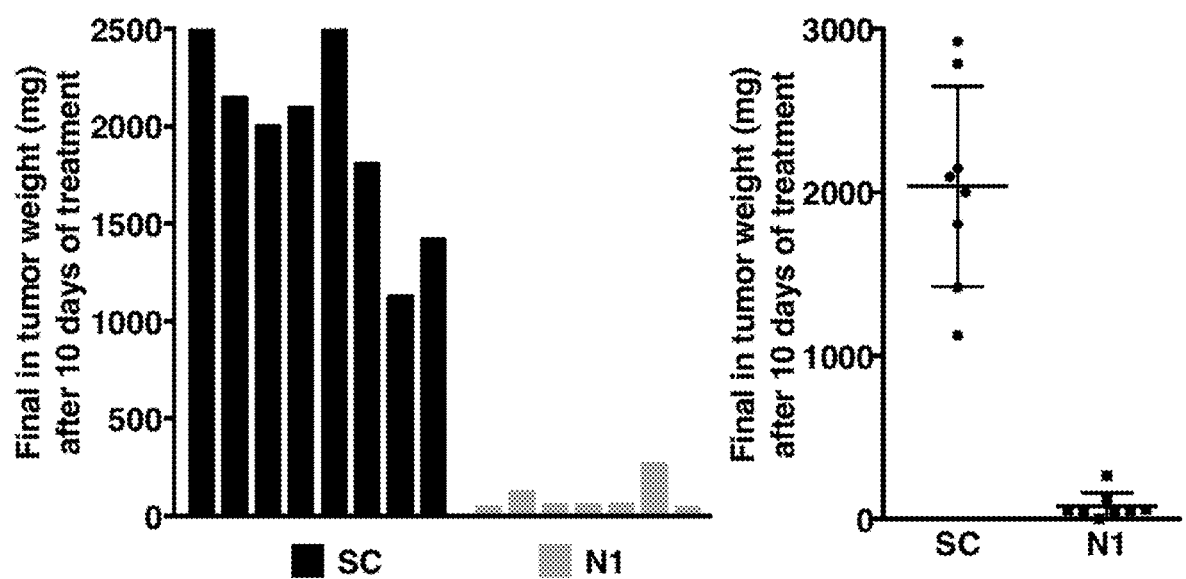
Figure 19A:
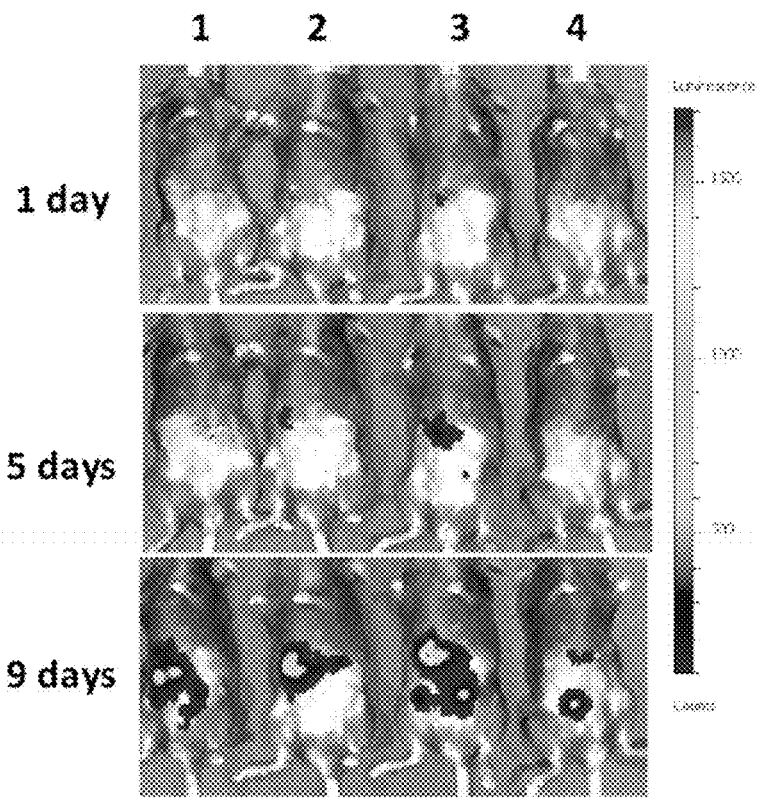
FIG. 19A-19B exemplify tumor growth in mice injected with B16F10 mouse melanoma cells expressing luciferase followed in vivo by optical imaging. B16F10 mouse melanoma cells expressing luciferase were injected subcutaneously in NOD-SCID immunodeficient mice. Tumor development and growth was followed over time by live optical imaging with Xenogen systems (FIG. 19A).
Figure 19B:
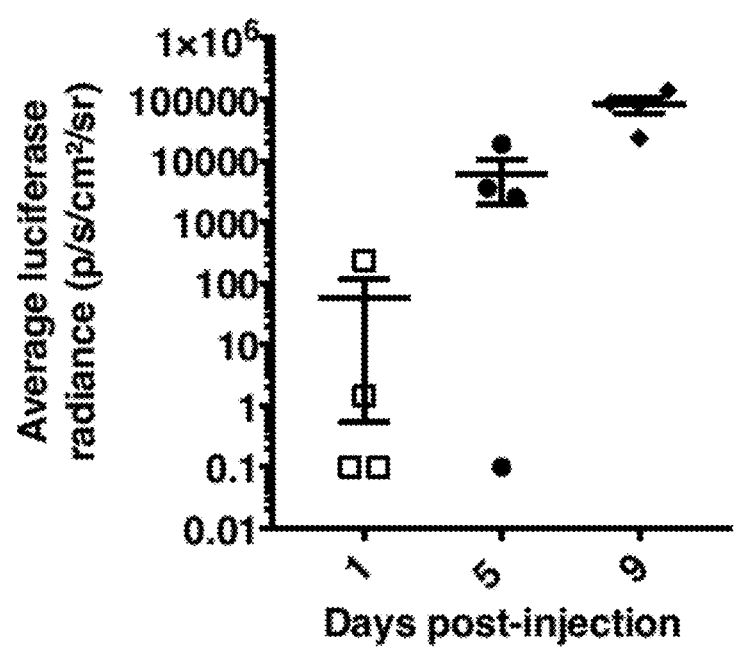
Figure 20:
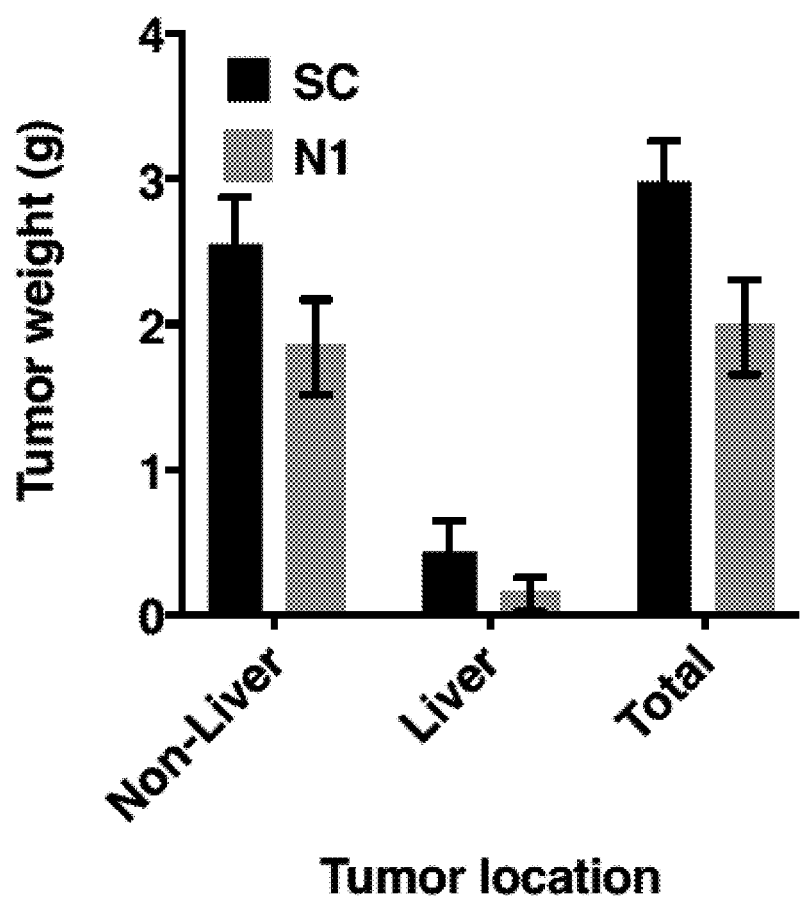
FIG. 20 illustrates B16F10 mouse melanoma cells injected in the liver of wild type mice to generate liver-associated tumors. Tumors were allowed to grow and mice were injected with Control (SC) or Nup160 (N1) siRNAs mixed with the Invivofectamine siRNA delivery system for 2 weeks for in vivo knockdown. Tumor size in liver and non-liver (metastasis) organs was determined by measuring tumor weight at the end of the experimental time.
Figure 21A:
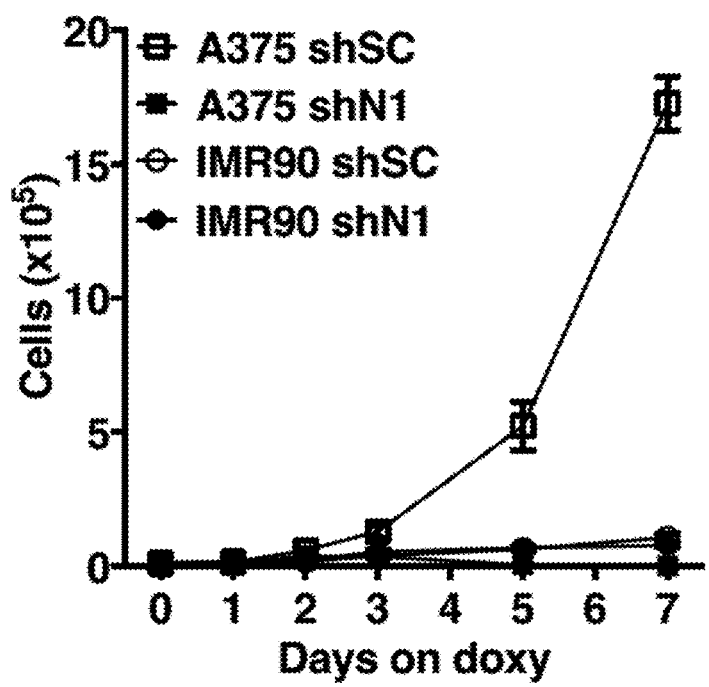
FIG. 21A-21B exemplify inhibition of nuclear pore assembly has a lower effect on normal cells compared to cancer cells. Melanoma cancer cells (A375) or normal fibroblasts (IMR90) were treated with shRNAs to inhibit nuclear pore assembly (shN1) and cell proliferation over time was compared to control-treated cells (shSC).
Figure 21B:
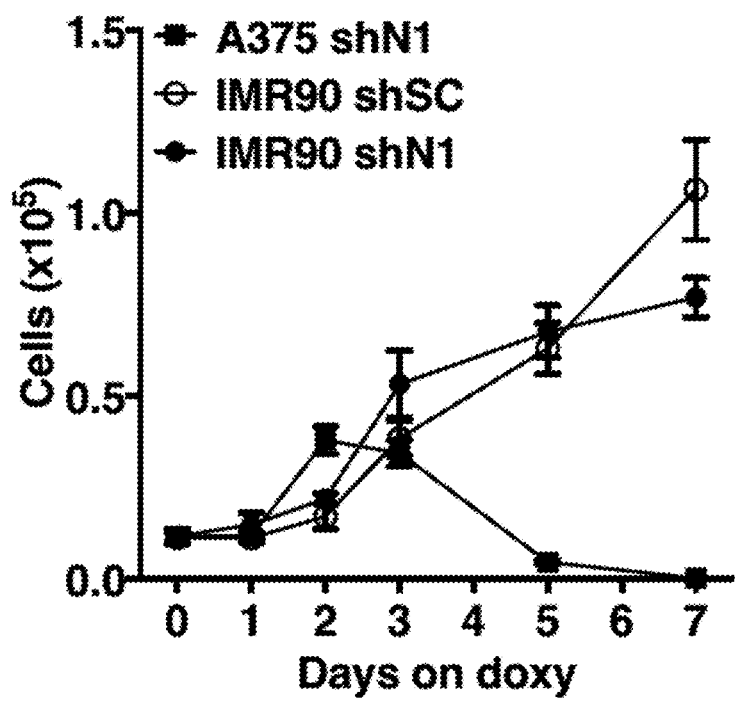
Figure 22A:
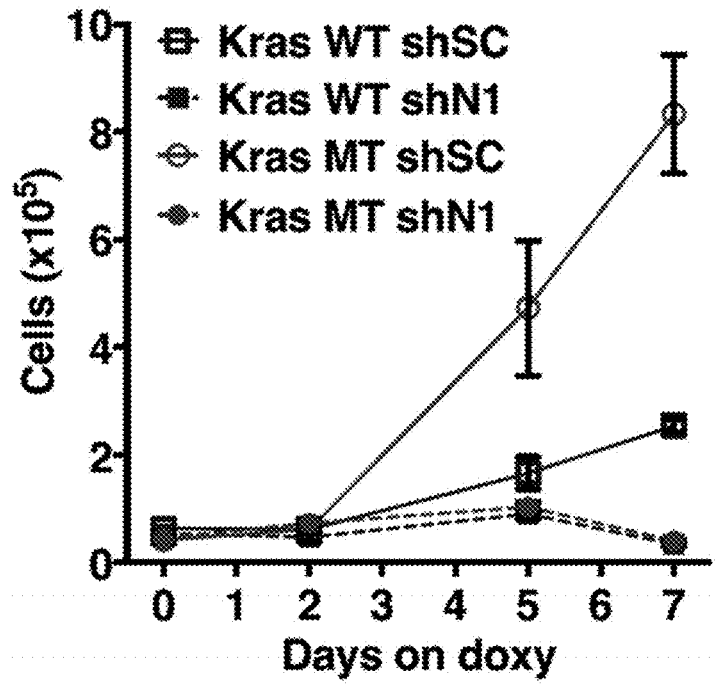
FIG. 22A-22B exemplify cancer cells carrying Ras mutation (G12D) are more sensitive to the inhibition of nuclear pore assembly.
Figure 22B:
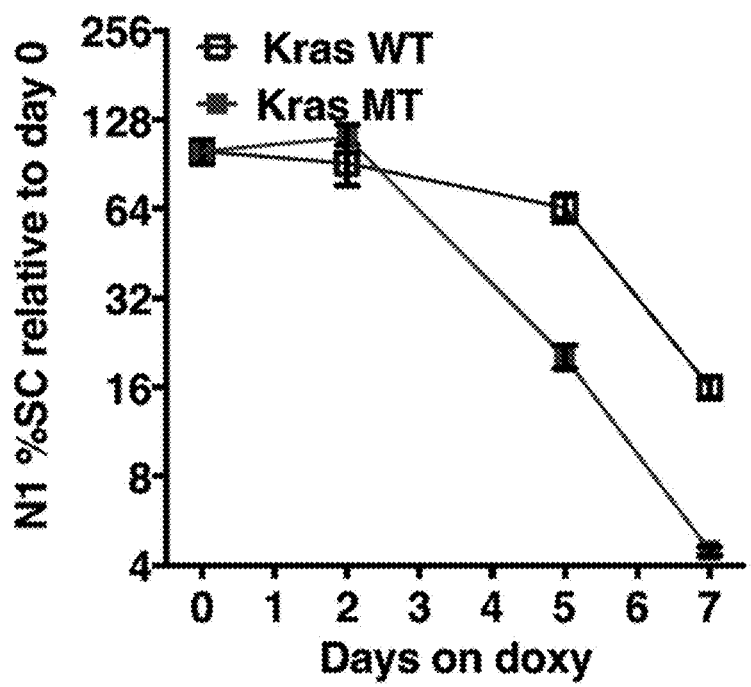
Figure 23:
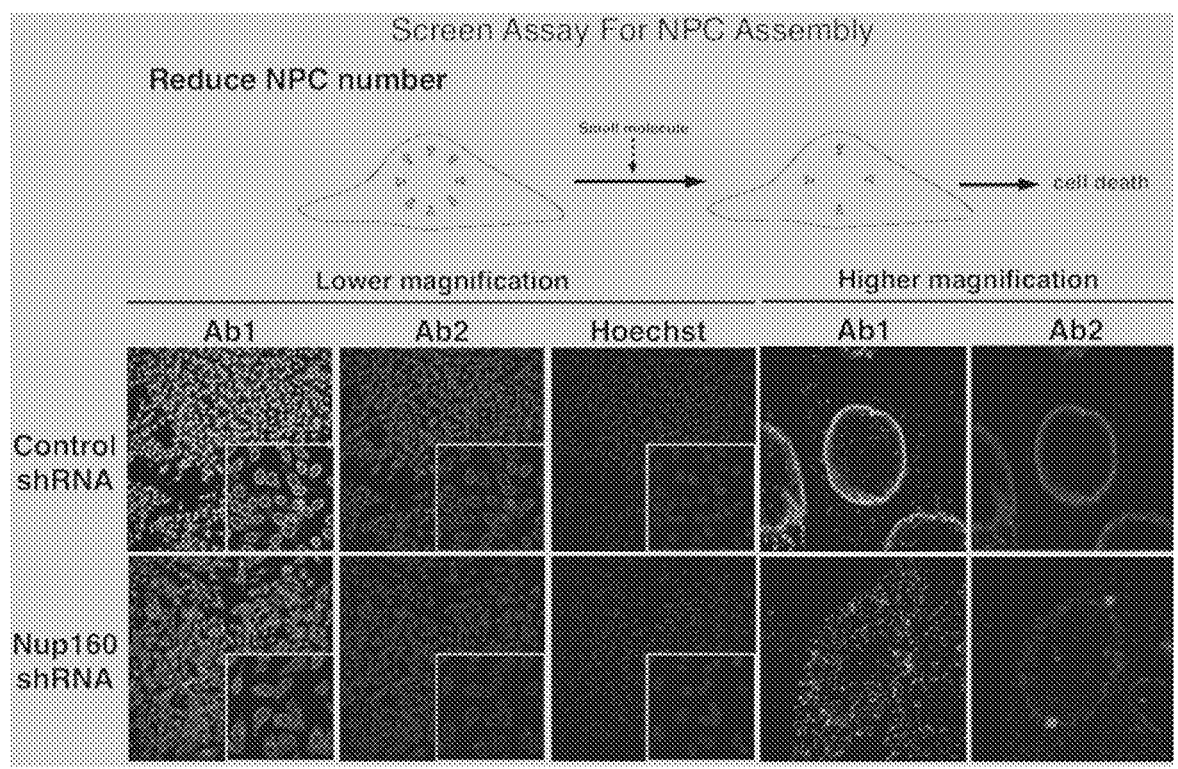
FIG. 23 exemplifies a detectable reduction in nuclear pore complex signal when nuclear pore complex assembly is inhibited.

Dividing cells expressing Control or Nup160 inducible shRNAs were seeded at low density and shRNA expression was induced by doxycycline. Cells were allowed to grow and divide and nuclear pore complex were stained with two different antibodies. FIG. 23 illustrates a detectable reduction in nuclear pore complex signal when nuclear pore complex assembly is inhibited. Nuclear pore complex inhibition is followed by quantifying the decrease in the signal at the nuclear periphery (FIG. 10) and/or by increase in the cytoplasmic aggregates that result from nuclear pore complex assembly inhibition.

Example 17. Tagging Endogenous Nucleoporins

Cells expressing an endogenous nuclear pore complex component tagged with GFP using CRISPR technology were imaged by confocal microscopy. Tagging of endogenous nucleoporins is used to detect nuclear pore complexes in the screen for nuclear pore complex assembly regulators instead of using antibodies. Using cell lines with endogenously tagged nuclear pore complex components also allow for screens to be performed in live cells.

Example 18. Analysis of Tumor Formation, Growth, Metastasis and Remission in Mice In these assays cancer formation is induced in mice and cancer development (tumor growth and metastasis) in control or treated mice is followed over time. For cancer induction, mice are injected with cancer cells subcutaneously or in specific tissues, such as liver or blood. Alternatively, tumors are induced chemically (e.g. as liver tumors with DEN, Aflatoxin or CCL4), or genetic models of cancer (e.g. p53 knockout, Ink4a/Arf knockout, PTEN knockout, activating kRas (G12D) mutant expressing mice or Myc oncogene expressing mice) are used to induce tumors in mice. Animals that develop cancer are treated with nuclear pore complex (NPC) assembly and disassembly regulators including but not limited to small molecules, siRNAs, shRNAs, microRNAs, mRNAs, gRNA/CRISPR and tumor growth is followed over time by measuring tumor size (or by blood analyses for blood malignancies such as leukemias and lymphomas). Alternatively, cancer cells expressing a luciferase or another bioluminescent reporter or fluorescent reporter are used to generate tumors and tumor growth and metastasis are followed by in vivo optical imaging such as Xenogen, IVIS® Spectrum, NightOWL LB 983, CRi Maestro 2, or other animal imaging systems. After treatment, tumors are collected, weighted, and the number of NPCs is analyzed in isolated tissues, cells and nuclei from the tumors by microscopy analysis using antibodies against nuclear pore complex component or by measuring the protein or RNA levels of nuclear pore complex proteins in tumors or cell extracts.

Example 19. In Vivo Analysis of Tumor Development

In these assays mice are injected with cancer cells subcutaneously or in specific tissues, such as liver or blood. Alternatively, tumors are induced chemically (e.g. as liver tumors with DEN, Aflatoxin or CCL4), or genetic models of cancer (e.g. p53 knockout, Ink4a/Arf knockout, PTEN knockout, activating kRAS (G12D) mutant expressing mice or Myc oncogene expressing mice) are used to induce tumors in mice. Mice are treated with nuclear pore complex (NPC) assembly and disassembly regulators including but not limited to small molecules, siRNAs, shRNAs, microRNAs, mRNAs, gRNA/CRISPR and the development of cancer is detected by analyzing is tumor size (or by blood analyses for blood malignancies such as leukemias and lymphomas). Alternatively, cancer cells expressing a luciferase or another bioluminescent reporter or fluorescent reporter are used for injections and tumor development is followed by in vivo optical imaging such as Xenogen, IVIS® Spectrum, NightOWL LB 983, CRi Maestro 2, or other animal imaging systems. After treatment, tumors are collected, weighted, and the number of NPCs is analyzed in isolated tissues, cells and nuclei from the tumors by microscopy analysis using antibodies against nuclear pore complex component or by measuring the protein or RNA levels of NPC proteins in tumors or cell extracts.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a proliferative disease or disorder in an individual in need thereof, the method comprising:
administering to the individual a therapeutically effective amount of an agent that inhibits nuclear pore complex assembly or induces nuclear pore complex disassembly, wherein the nuclear pore complex assembly is not inhibited in non-dividing cells or the nuclear pore complex disassembly is not induced in the non-dividing cells, wherein the proliferative disease or disorder is cancer, wherein the cancer has a mutation in a Ras gene, wherein the agent is a small interfering RNA (siRNA) or short hairpin RNA (shRNA), and wherein the agent targets one or more of Nup93 or Nup96 of a nuclear pore complex.

2. The method of claim 1, wherein the agent inhibits expression of Nup93 or Nup96 of the nuclear pore complex.

3. The method of claim 1, wherein the agent promotes degradation of Nup93 or Nup96 of the nuclear pore complex.

4. The method of claim 1, wherein the mutation is a G12D mutation.

5. The method of claim 1, wherein the cancer is melanoma.

6. A method of treating a proliferative disease or disorder in an individual in need thereof, the method comprising:
administering to the individual a therapeutically effective amount of an agent that inhibits nuclear pore complex assembly or induces nuclear pore complex disassembly, wherein the nuclear pore complex assembly is not inhibited in non-dividing cells or the nuclear pore complex disassembly is not induced in the non-dividing cells, wherein the proliferative disease or disorder is cancer, wherein the cancer has a mutation in a Ras gene, wherein the agent is a small interfering RNA (siRNA) or short hairpin RNA (shRNA), and wherein the agent targets one or more of Nup93 or Nup96 of a nuclear pore complex, and wherein the cancer is colorectal cancer.

7. The method of claim 1, wherein the agent inhibits Nup96 of the nuclear pore complex.

8. The method of claim 1, wherein the agent is small interfering RNA (siRNA).

9. The method of claim 1, wherein the agent is short hairpin RNA (shRNA).

10. A method of treating a proliferative disease or disorder in an individual in need thereof, comprising:
administering to the individual a therapeutically effective amount of an agent that inhibits nuclear pore complex assembly or induces nuclear pore complex disassembly, wherein the nuclear pore complex assembly is not inhibited in non-dividing cells or the nuclear pore complex disassembly is not induced in the non-dividing cells, wherein the proliferative disease or disorder is cancer, wherein the cancer has a mutation in a Ras gene, and wherein the agent targets one or more of Nup93 or Nup96 of a nuclear pore complex, and wherein the agent is a small molecule or an antisense oligonucleotide.

11. The method of claim 1, further comprising administering an additional therapeutic agent.

12. The method of claim 1, wherein the administering to the individual the therapeutically effective amount of the agent comprises contacting a cell having a number of nuclear pore complexes with the agent, wherein the agent reduces the number of nuclear pore complexes in the cell.

13. The method of claim 1, wherein the agent inhibits Nup93 of the nuclear pore complex.

* * * * *